United States Patent [19]

LeSuer

[11] Patent Number: 5,041,622

[45] Date of Patent: Aug. 20, 1991

[54] THREE-STEP PROCESS FOR MAKING SUBSTITUTED CARBOXYLIC ACIDS AND DERIVATIVES THEREOF

[75] Inventor: William M. LeSuer, Cleveland, Ohio

[73] Assignee: The Lubrizol Corporation, Wickliffe, Ohio

[21] Appl. No.: 619,811

[22] Filed: Nov. 28, 1990

[51] Int. Cl.$^5$ .................................................. C07C 51/00
[52] U.S. Cl. .................................. 560/190; 252/56 R; 549/255; 562/595
[58] Field of Search ................ 560/190; 549/255; 562/595; 252/56 R

[56] References Cited

U.S. PATENT DOCUMENTS

| | | | |
|---|---|---|---|
| 2,588,412 | 3/1952 | Rocchini | 252/51.5 |
| 2,858,329 | 10/1958 | Brazten | 260/485 |
| 2,891,786 | 6/1959 | Stewart | 252/51.5 |
| 3,024,195 | 3/1962 | Drummond et al. | 252/51.5 |
| 3,087,936 | 4/1963 | Le Suer | 260/326.3 |
| 3,125,503 | 2/1966 | Vries | 252/51.5 |
| 3,163,603 | 12/1964 | LeSuer | 252/33.6 |
| 3,172,892 | 3/1965 | Le Suer et al. | 260/326.5 |
| 3,184,474 | 5/1965 | Catto et al. | 260/326.3 |
| 3,194,812 | 7/1965 | Norman et al. | 260/326.5 |
| 3,200,107 | 8/1965 | Le Suer | 260/132 |
| 3,202,678 | 8/1965 | Stuart et al. | 260/326.5 |
| 3,210,283 | 10/1965 | Stuart et al. | 252/51.5 |
| 3,214,460 | 10/1965 | McGee et al. | 260/482 |
| 3,215,707 | 11/1965 | Rense | 260/326.3 |
| 3,216,936 | 11/1965 | Le Suer | 252/32.7 |
| 3,219,666 | 11/1965 | Norman et al. | 260/368 |
| 3,220,949 | 11/1965 | Bell Jr. et al. | 252/51.5 |
| 3,231,587 | 1/1966 | Rense | 260/346.8 |
| 3,252,908 | 5/1966 | Coleman | 252/31 |
| 3,255,108 | 6/1966 | Wiese | 252/32.7 |
| 3,256,185 | 6/1966 | Le Suer | 252/32.7 |
| 3,269,946 | 8/1966 | Wiese | 252/32.5 |
| 3,272,746 | 9/1966 | Le Suer et al. | 252/47.5 |
| 3,274,113 | 9/1966 | Reiland Jr. | 252/78 |
| 3,288,577 | 11/1966 | Patinkin et al. | 44/62 |
| 3,306,908 | 2/1967 | Le Suer | 260/326.3 |
| 3,311,558 | 3/1967 | Prizer et al. | 252/47.5 |
| 3,311,561 | 3/1967 | Anderson et al. | 252/75 |
| 3,312,619 | 4/1967 | Vloryard | 252/47.5 |
| 3,324,053 | 6/1967 | Knapp | 252/51.5 |
| 3,331,776 | 7/1967 | Krukziener | 252/56 |
| 3,341,542 | 9/1967 | Le Suer et al. | 260/268 |
| 3,364,001 | 1/1968 | Drummond et al. | 44/71 |
| 3,366,569 | 1/1968 | Norman et al. | 252/51.5 |
| 3,367,943 | 2/1968 | Miller et al. | 260/326.3 |
| 3,373,111 | 3/1968 | Le Suer et al. | 252/51.5 |
| 3,379,515 | 4/1968 | Lindstrom et al. | 44/62 |
| 3,381,022 | 4/1968 | Le Suer | 260/404.8 |
| 3,389,087 | 6/1968 | Kresge et al. | 252/59 |
| 3,390,086 | 6/1968 | O'Halloran | 252/47.5 |
| 3,399,141 | 8/1968 | Clemens | 252/47.5 |
| 3,401,118 | 9/1968 | Benolt Jr. | 252/51.5 |
| 3,413,104 | 11/1968 | Mehmedbasich | 44/62 |
| 3,427,245 | 2/1969 | Hotten | 252/34.7 |
| 3,438,899 | 4/1969 | Benolt Jr. | 252/51.5 |
| 3,444,082 | 5/1969 | Kautsky | 252/51.5 |
| 3,448,049 | 6/1969 | Preuss et al. | 252/51.5 |
| 3,450,715 | 6/1969 | Lindstrom et al. | 260/326.3 |
| 3,451,933 | 6/1969 | Lester | 252/51.5 |
| 3,452,002 | 6/1969 | Brasch | 260/239.3 |
| 3,454,496 | 7/1969 | Schlobohm | 252/32.7 |
| 3,455,827 | 7/1969 | Mehmedbasich et al. | 252/32.7 |
| 3,476,686 | 11/1969 | Verdol et al. | 252/51.5 |
| 3,502,677 | 3/1970 | Le Suer | 260/268 |
| 3,505,227 | 4/1970 | Lowe | 252/51.5 |
| 3,522,179 | 7/1970 | Le Suer | 252/51.5 |
| 3,523,768 | 8/1970 | Mehmedbasich et al. | 44/62 |
| 3,525,693 | 8/1970 | Lyle et al. | 252/34 |
| 3,544,467 | 12/1970 | Kautsky | 252/51.5 |
| 3,573,205 | 3/1971 | Lowe et al. | 252/51.5 |

(List continued on next page.)

FOREIGN PATENT DOCUMENTS 1024906 9/1963 United Kingdom .
1492337 11/1977 United Kingdom .

OTHER PUBLICATIONS

Information Disclosure Statement Under 37 CFR 1.97-1.99, Filed During Prosecution of U.S. Case patent application, Ser. No. 578,713 Filed Feb. 9, 1984.
Search Report From PCT Application International Publication Number WO85/03504 International Publication Date Aug. 15, 1985.
International Search Report for PCT International Application PCT/US85/00090.

*Primary Examiner*—Jacqueline V. Howard
*Attorney, Agent, or Firm*—Frederick D. Hunter; Forrest L. Collins; Robert A. Franks

[57] ABSTRACT

An improvement in known processes for preparing substituted carboxylic acids useful as acylating agents which comprise reacting (A) at least one aliphatic polymer of one or more lower olefins with (B) an acidic reactant selected from the group consisting of fumaric acid, itaconic acid, maleic acid, and the corresponding anhydrides, lower alkyl esters, acyl chlorides and acyl bromides, in the presence of chlorine can be improved by the steps of (i) reacting at a temperature of about 100°-200° C., a mixture of (A) and (B) in the presence of about 0.05 to 0.15 equivalent of chlorine per equivalent of (A) until all of the chlorine has reacted to provide a first intermediate product (ii) continuing the reaction in the absence of chlorine at a temperature of from about 180°-250° C. until a conversion of 0.4 to 1.1 equivalents of (B) per equivalent of (A) is attained to provide a second intermediate product, and (iii) reacting said second intermediate with about 0.2 to 1.5 equivalents of chlorine per equivalent of (A) used in step (i) at a temperature of about 180°-225° C. The carboxylic acids produced by this improved process can be used, per se, in lubricants and fuels and as acylating agents in reactions with amines, alcohols, reactive metals or reactive metal compounds to form derivative products which are useful, for example, as additives for lubricants and normally liquids fuels.

16 Claims, No Drawings

U.S. PATENT DOCUMENTS

| | | | |
|---|---|---|---|
| 3,575,743 | 4/1971 | Widmer et al. | 252/51.5 |
| 3,576,743 | 4/1971 | Widmer et al. | 252/51.5 |
| 3,585,194 | 6/1971 | Leister | 260/268 |
| 3,629,119 | 12/1971 | Weaver | 252/77 |
| 3,630,904 | 12/1971 | Musser et al. | 252/51.5 |
| 3,632,511 | 1/1972 | Liso | 252/51.5 |
| 3,652,616 | 3/1972 | Watson et al. | 260/429 |
| 3,658,707 | 4/1972 | Delsfield et al. | 252/51.5 |
| 3,679,585 | 7/1972 | Brook et al. | 252/51.5 |
| 3,687,644 | 8/1972 | Delafield et al. | 44/56 |
| 3,697,428 | 10/1972 | Maeinhardt et al. | 252/56 |
| 3,708,522 | 1/1973 | Le Suer | 260/485 |
| 3,749,695 | 7/1973 | de Vries | 252/47.5 |
| 3,764,536 | 10/1973 | Hellmuth et al. | 252/49.7 |
| 3,783,131 | 1/1974 | Le Suer | 252/34.7 |
| 3,795,495 | 3/1974 | Howland et al. | 44/58 |
| 3,833,624 | 9/1974 | Bork | 260/404.5 |
| 3,846,093 | 11/1974 | Feldman | 44/62 |
| 3,897,456 | 7/1975 | Brewster | 260/340.2 |
| 3,910,776 | 10/1972 | Feldman | 44/62 |
| 3,912,764 | 10/1975 | Palmer Jr. | 260/346.8 |
| 3,950,341 | 4/1976 | Nobukazu et al. | 260/268 |
| 3,966,620 | 6/1976 | Bridger et al. | 252/33.4 |
| 4,048,080 | 9/1977 | Lee et al. | 252/51.54 |
| 4,098,585 | 7/1978 | Vartanian et al. | 44/63 |
| 4,102,798 | 7/1978 | Ryer et al. | 252/51.5 |
| 4,110,349 | 8/1978 | Cohen | 260/533 R |
| 4,113,639 | 9/1978 | Lonstrup et al. | 252/51.5 |
| 4,147,520 | 4/1979 | Ilnyckyj | 44/62 |
| 4,148,605 | 4/1979 | Andress Jr. | 422/7 |
| 4,185,485 | 1/1980 | Schick et al. | 72/42 |
| 4,199,462 | 4/1980 | Soula et al. | 252/51.5 |
| 4,211,534 | 7/1980 | Feldman | 44/62 |
| 4,234,435 | 4/1981 | Meinhardt et al. | 252/46.6 |
| 4,257,779 | 3/1981 | Sung et al. | 44/63 |
| 4,486,573 | 12/1984 | Hayashi | 525/285 |

THREE-STEP PROCESS FOR MAKING SUBSTITUTED CARBOXYLIC ACIDS AND DERIVATIVES THEREOF

This is a continuation of copending application(s) Ser. No. 07/185,213 filed on Apr. 22, 1988, now abandoned, which is a continuation of Ser. No. 06/854,378 filed on Apr. 21, 1986, now abandoned and a division of Ser. No. 06/578,713 filed on Feb. 21, 1984, now abandoned.

FIELD OF THE INVENTION

This invention relates to an improved process for preparing substituted carboxylic acids from aliphatic polymers of lower olefins and acidic reactants such as maleic anhydride. More specifically, it relates to an improved three-step process for preparing such acids using reduced amounts of chlorine.

BACKGROUND OF THE INVENTION

Carboxylic acids substituted with substantially aliphatic substituents derived from polymerization of lower olefins have been described in the prior art and have many important industrial uses. For example, they can be used as anti-rust agents in various organic media such as normally liquid fuels and lubricating oils. They can also serve as intermediates for the formation of metal salts, esters, and nitrogen-containing products which are useful as viscosity index improvers, dispersants, etc., for oil-based lubricants and normally liquid fuels.

Such carboxylic acids can be prepared by thermally reacting an aliphatic hydrocarbon or halogenated aliphatic hydrocarbon with unsaturated acids or acid derivatives at a temperature above about 200° C. The hydrocarbon typically is an olefin polymer such as polypropene or polybutene having a number average molecular weight above about 200. The rate of conversion of such reactions, however, is low and attempts to improve the conversion rate by increasing the reaction temperature and/or using super-atmospheric pressure results in degradation of maleic anhydride to useless carbon dioxide, water and tarry solids. This results in both waste of the valuable maleic anhydride and contamination of the acylating agent that has been produced.

One method for improving the conversion rate, particularly when using an aliphatic hydrocarbon alkylating agent, involves carrying out the reaction in the presence of chlorine. In many instances, high temperatures and long reaction times are still required. These facts, coupled with the necessity for the use of chlorine which is relatively dangerous to use, as well as being expensive and sometimes in short supply, make it desirable to develop alternative methods for the preparation of substituted carboxylic acids or derivatives, which methods are more economical in their use of chemicals and energy.

One such method has been described in U.S. Pat. No. 3,912,764. It comprises a two-stage process in which an olefin polymer is first caused to undergo a thermal reaction with maleic anhydride to a point short of conversion of all of said maleic anhydride, and subsequently an amount of chlorine less than one mole for each remaining mole of maleic anhydride is added, and the reaction is continued in the presence of said chlorine. While this process is said to be more economical than those previously known since it uses a omical than those previously known since it uses a relatively small amount of chlorine and, to a large extent, can be carried out at relatively low temperatures, it is inefficient in that the product is described as containing on the order of 30% unreacted olefin polymer.

Another process for preparing substituted carboxylic acids is by the reaction of a halogenated high molecular weight polymer of one or more lower olefins with an acidic reagent such as maleic anhydride. Such halogenated polymers are usually made by halogen treatment of a hydrocarbon polymer itself and their production requires an average of at least one mole of halogen per mole of hydrocarbon polymer.

A variant of the halogenated hydrocarbon route to succinic acid acylating agents is the process disclosed in U.S. Pat. Nos. 3,215,707 and 3,231,587. This process comprises first preparing a mixture of high molecular weight hydrocarbon polymer and maleic anhydride and then contacting this mixture, at a temperature of about 140° C. to about 250° C., with at least one mole of chlorine for each mole of maleic anhydride present. The reaction takes place over a period of five hours or more. This process also requires the use of large amounts of chlorine relative to the amount of maleic anhydride incorporated. Since it is well known that chlorine is highly corrosive towards many materials normally used to construct large scale reactors, the presence of large amounts of chlorine usually necessitates the use of special reactor equipment fabricated from high-cost materials. Often the final products from such reactions contain at least 0.4% residual chlorine, which is unnecessary to their function as additives or additive intermediates and may, in some instances, be detrimental to their function.

Published French Application 2,201,309 describes a two-stage process wherein in the first stage an olefin polymer is reacted thermally with maleic anhydride to a point well short of conversion of all the maleic anhydride. In the second stage, an amount of chlorine less than one mole for each mole of maleic anhydride is introduced into the polymer/anhydride mixture to complete the reaction. The product mixtures resulting from this process are described as containing more than 30% unreacted olefin polymer. Since the presence of unreacted olefin polymer in the succinic acid acylating reagents used in commerce performs no known useful function, the process of the '309 published application results in the loss of a valuable petrochemical intermediate. This is particularly true since neither the 309 published application nor the general prior art disclose efficient, economical means for separating unreacted olefin polymer from such carboxylic acids.

In U.S. Pat. No. 4,110,349, substituted carboxylic acids of the type prepared by the alkylation of maleic anhydride with an olefin polymer (e.g., polybutene) are prepared by a two-step method which is more economical and efficient than previously known methods. In the first step, the alkylating hydrocarbon is reacted with an unsaturated dicarboxylic acid or derivative thereof in an amount of the latter equal to about 30-90% by weight of the amount required to afford the desired product, optionally in the presence of a small amount of chlorine. In the second step, additional acid or derivative thereof is added and the reaction is continued in the presence of added chlorine.

SUMMARY OF THE INVENTION

The present invention is directed to an improvement in the art of producing substituted carboxylic acids from aliphatic polymers of lower olefins and acidic reactants, such as maleic anhydride, which offer the advantages of low chlorine consumption and high conversion of both maleic anhydride and olefin polymer reactants.

Briefly, this invention involves:

In a method for preparing substituted carboxylic acids or derivatives thereof which comprises reacting (A) at least one aliphatic polymer of a lower olefin (B) at least one acidic reactant selected from the group consisting of fumaric acid; itaconic acid; maleic acid; and the anhydrides, lower alkyl esters, acyl chlorides and acyl bromides of any of these acids, at least a part of the reaction taking place in the presence of chlorine, the improvement comprising the steps of (i) reacting at a temperature of about 100°–200° C. a mixture of (A) and (B) in the presence of about 0.05 to 0.15 equivalent of chlorine per equivalent of (A) until all of the chlorine has reacted to provide a first intermediate product, (ii) continuing the reaction in the absence of chlorine at a temperature of from about 180°–250° C. until a conversion of 0.4 to 1.1 equivalents of (B) per equivalent of (A) is attained to provide a second intermediate product, (iii) reacting said second intermediate with about 0.2 to 1.5 equivalents of chlorine per equivalent of (A) used in step (i) at a temperature of about 180°–225° C.

DETAILED DESCRIPTION OF THE INVENTION

The substituted carboxylic acids of this invention are prepared from (A) at least one aliphatic polymer of at least one lower olefin, and (B) at least one acidic reactant of the type described hereinafter. The description of these polymers as being aliphatic is intended to include polymers that are substantially aliphatic and which contain no more than 10% non-aliphatic carbon atoms, that is, carbon atoms which are part of an alicyclic ring. Thus, a polymer containing, e.g., 5% of its carbon atom in alicyclic ring structures and 95% of its carbon atom in aliphatic structures would be an aliphatic polymer within the context of this invention. The aliphatic polymers may also contain, and preferably will contain an olefinic bond. More preferably, the polymers will contain no more than one olefinic or acetylenic carbon-carbon bond for every ten carbon-carbon bonds in the molecule.

The lower olefins from which the aliphatic polymers (A) of this invention are made are those containing up to seven carbon atoms. These olefins can be mono- or diolefins; the latter can be conjugated or non-conjugated. Preferably, the olefins used to prepare the polymers used are monoolefins. More preferably, they are mono-1-olefins, and most preferably, they are $C_{2-6}$ mono-1-olefins.

Exemplary of the lower olefins which can be used to prepare the aliphatic polymers (A) of this invention are ethylene, propylene, 1- and 2-butene, isobutene, the pentenes (all aliphatic isomers), the hexenes (all aliphatic isomers) and the heptenes (all aliphatic isomers).

Among the conjugated lower diolefins which can be used to prepare the polymers (A) of this invention, are butadiene, isoprene, 1,3-pentadiene and 1,3-hexadiene; non-conjugated olefins include 1,4-pentadiene, 1,4-hexadiene, 1,5-hexadiene, etc.

Preferred monoolefins for the preparation of the aliphatic polymers of this invention are ethylene, propylene, 1- and 2-butene, and especially isobutene. Preferred conjugated lower olefins which can be used to prepare the polymers (A) used in this invention include butadiene and isoprene (2-methyl-1,4-butadiene), while the preferred non-conjugated lower olefins which can be used to prepare the polymers (A) and 1.4-hexadiene and 1,4-pentadiene.

The aliphatic polymers (A) used in this invention can be homo- or interpolymers. If they are of the latter type, they can be co-, ter-, tetra-, etc., polymers and they can be ordinary chain interpolymers or graft copolymers. In general, homopolymers are preferred, although copolymers such as ethylene/propylene copolymers and terpolymers and interpolymers made from monomers having the same carbon content, such as 1,cis-2,trans-2, and isobutene are often used.

As noted above, the aliphatic polymers (A) used in this invention can contain small amounts of alicyclic or aromatic carbon atoms. Such alicyclic and aromatic carbon atoms can be derived from such monomers as cyclopentene, cyclohexene, methylene cyclopentene, methylene cyclohexene, 1,3-cyclohexadiene, norbornene, norbornadiene, cyclopentadiene styrene and alpha-methyl styrene.

The aliphatic polymers (A) used in this invention generally contain more than about 30 aliphatic carbon atoms; preferably, they contain less than 300 carbon atoms; more preferably, they contain at least 50 aliphatic carbon atoms and less than about 250 carbon atoms. In terms of molecular weight, the polymers used in this invention (A) have number average molecular weights (as determined by gel permeation chromatography) of at least about 420, more preferably, they have a maximum number average molecular weight (as determined by gel permeation chromatography) of no more than about 10,000. A particularly preferred range of number average molecular weights is from about 500 to about 3,000.

A particularly preferred class of aliphatic polymers (A) for use in this invention are the polybutenes, that is polymers prepared by polymerization of one or more of the butenes. Polyisobutenes are especially preferred; these polymers are well known commercial materials and are made from isobutene streams containing substantial amounts of isobutene itself. Often these streams contain other $C_4$ olefins such as 1-butene, cis- and trans-2-butene and minor amounts of butadiene which may or may not be incorporated in the polymer. The polyisobutene polymers have predominantly isobutene derived units, i.e., units of the structure

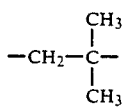

Usually these units constitute at least 80%, preferably at least 90% of the polyisobutene (in terms of number of carbon atoms present). These polyisobutenes are well known to those of skill in the art and further details concerning their structure and preparation can be found in U.S. Pat. Nos. 3,215,707; 3,231,587; 3,515,669; and 3,579,450. These U.S. patents are hereby incorporated by reference for their disclosures relative to the nature and production of the aliphatic polymers (A) used in the present invention.

The acidic reactant (B) used in the present invention is selected from the group consisting of fumaric acid, itaconic acid, maleic acid, and the anhydrides lower alkyl esters, acyl chlorides and acyl bromides of these acids. The lower alkyl esters and acyl chlorides and bromides of fumaric acid, itaconic acid and maleic can be the so-called half-esters or half-acyl chlorides, etc., having but one of the two carboxyl groups converted to the main derivative or they can be the diesters, diacyl chlorides, etc.

The preferred acidic reactants (B) used in the process of this invention are maleic acid compounds selected from the formula consisting of:

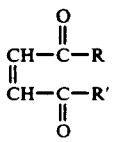

wherein R and R' are each independently selected from the group consisting of —OH, —O—lower alkyl, —Cl and —Br, or R and R' taken together may be —O—. Maleic anhydride is an especially preferred acidic reactant (B). The lower alkyl groups referred to above in the description of the acidic reactant (B) are those containing from one to seven carbon atoms, such as methyl, ethyl, propyl (both isomers), butyl (all isomers), pentyl (all isomers), hexyl (all isomers), and heptyl (all isomers).

The acidic reactant (B) can comprise mixtures of two or more of any of the afore-described acidic reactants. Thus, for example, a mixture of fumaric acid and maleic anhydride can be used as can a mixture of diethyl fumarate and itaconic acyl monochloride. Similarly, mixtures of maleic anhydride with its monolower alkyl esters can be used as can be mixtures of maleic anhydride with its di-lower alkyl esters. Use of such mixtures is sometimes convenient because of their availability and relatively low cost. Naturally, the pure compounds themselves can also be used where desired.

As is explained above, the reaction of admixtures of the aliphatic polymer (A) and acidic reactant (B) at temperatures above 140° C. is a known process for preparing substituted succinic acid acylating agents. In the conventional known processes. the admixture is heated either in the absence or presence of a total of up to one or more moles of chlorine for each mole of acidic reactant present in the initial admixture. When the chlorine is omitted, higher temperatures are required and the reaction takes longer.

In the present invention, however, an initial admixture of polymer and acid reactant is prepared, and a small amount of chlorine is introduced into the admixture. Amounts in the range of 0.05 to 0.15, and preferably 0.08 to 0.12 equivalent of chlorine per equivalent of polymer (A) generally are used. The temperature of the mixture is raised to, and maintained at a temperature within the range of 110°-190° C. until all of the chlorine has reacted and the evolution of hydrogen chloride has ceased. In a preferred embodiment, the chlorine is not introduced until the initial admixture is at a temperature of at least about 100°-110° C. The newly formed reaction mixture (i.e., that containing chlorine) is then heated up to a temperature of about 190° C. It is essential in the practice of the present invention that the total amount of chlorine introduced during this first step of the reaction is within the range of about 0.05 to 0.15 equivalent of chlorine for each mole of polymer reactant present in the initial admixture, and the particular amount used will be at least in part dependent on the amount of metal impurities contained in the polymer utilized. It has been found that if the metal is not deactivated by reaction with the chlorine, the presence of metal will effect an undesirable degradation of the acidic reactant (B) resulting in lower yields of desired product and increased production of undesirable side products.

The relative amounts of polymer (A) and acid (B) in the initial mixture and/or the amount used in the overall reaction will range, on an equivalent basis, from about 1:08 to 1:2. It is preferred, however, that the ratio be at least 1:1 to ensure that most, if not all of the polymer is utilized. Also, when it is desired to have more acidic groups in the product, ratios in excess of 1:1 are used.

The upper reaction temperature of the first step of the process of the invention is not critical and is only limited by the decomposition temperature of the intermediate products and the components of the reaction mixture. Preferably, however, the upper limit is around 200° C.

In various embodiments of the present invention, the chlorine can be introduced in different manners; for example, in a certain preferred embodiment, the chlorine is introduced continuously or intermittently over a period of time while increasing the reaction temperature to at least 190° C.

In other preferred embodiments of this invention, the chlorine can be introduced continuously, while raising the reaction temperature to an intermediate point such as at least about 175° C. In the alternative, the chlorine can be introduced intermittently while the temperature is increased to at least about 175° C. In either of these preferred embodiments the resulting reaction mixture is then maintained at a temperature of about 190°-200° C. Obviously, the reaction mixture can be elevated to such latter temperature while chlorine is being introduced and thereafter maintained at a temperature of about 200° C.

It is not necessary that all the chlorine used during the first step be introduced at a temperature below 190° C. Thus, it is possible to introduce some of the chlorine at a point after which the reaction temperature has reached about 190° C. as long as the total amount of chlorine introduced does not exceed 0.15 equivalent of chlorine for each equivalent of polymer reactant present in the initial reaction admixture.

Similarly, additional acidic reactant can be introduced into the reaction mixture before, during or after the period when the additional chlorine is introduced, with the proviso that the amount of acidic reactant does not exceed about 10% by weight of the total weight of acidic reactant present in the initial admixture.

Generally, the reaction time for the first step of this invention ranges from about 0.5 hour to about six to eight hours. Preferably, the reaction time ranges from about two to about five hours. As is apparent to those skilled in the art, the duration of the reaction will depend at least in part on such variables as the quantity of reactants, reaction temperature, and the like. In any event, the reaction should be conducted at least until the evolution of hydrogen chloride ceases.

The equivalent ratio of reagent (A) to reagent (B) in step (i) will vary according to the proportion of acid or acid derivative groups desired in the product. Typically, about 0.3 to 2.0 equivalents of reagent (B) can be used per equivalent of reagent (A). but it is generally desirable to use at least one equivalent of acid reagent (B) per equivalent of reagent (A) so as to minimize the amount of unreacted olefin polymer present in the product.

In the second step of the improved method of the invention, the first intermediate product produced in the first step is heated in the absence of chlorine at a temperature of from about 180°-250° C. to continue the alkylation reaction of acid (B) and to produce a second intermediate product. The alkylation reaction of this second step is continued until the desired extent of conversion is obtained. Generally heating is continued in the absence of chlorine until a conversion of about 0 4 to 1.1 equivalents of (B) per equivalent of (A) has been attained. The extent of conversion can be determined by methods known in the art. A preferred conversion range is from about 0.5 to 0.9 equivalent of (B) per equivalent of (A). The reaction time for the second step may vary from about 10 to about 25 hours or more. An essential feature of step (ii) is that the reaction is conducted in the absence of chlorine, and is generally conducted in an inert atmosphere such as under a positive nitrogen blanket. Temperatures between about 200° to about 225° C. are generally satisfactory and are preferred for step (ii).

When the desired second intermediate product is obtained in accordance with the procedure described above, the second intermediate product then is heated for an additional period in the presence of from about 0.2 to about 1.5 equivalents of chlorine per equivalent of the polymer used in step (i) while continuing to heat the reaction mixture at a temperature of about 180°-225° C. The chlorine may be added continuously or intermittently, although continuous addition of the chlorine over a period of time is preferred. After all of the chlorine is added, heating of the mixture is continued until the desired product is obtained. The point at which step (iii) is essentially complete can be determined by analyzing the reaction mixture for the percentage of acid be remaining and/or for the saponification number of the reaction product. When the reaction is completed, the reaction mixture preferably is blown with nitrogen while maintaining the reaction mixture at a temperature of 190° C.

Although the improved process of this invention involves three distinct steps, the process can be, and generally is conducted in the same reaction vessel. If desired, however, the intermediate product of step (i) and/or (ii) can be transferred to different reaction vessels for further reaction and processing.

The improved process of this invention can be carried out in the presence of a substantially inert, normally liquid solvent/diluent such as hydrocarbon mineral oils of lubricating oil viscosity, lower molecular weight hydrocarbon solvents such as benzene, toluene, xylene or xylene mixtures, petroleum naphtha, reformate, etc. However, solvents generally are not necessary. When volatile lower molecular weight hydrocarbon solvents are used, it is often preferably to carry out the reaction at pressures in excess of atmospheric. Generally, however, the reaction can be carried out at atmospheric pressure or at pressures ranging up to about five atmospheres. Further details as to the inert solvent/diluents which can be used in these reactions, as well as details as to reaction times and pressures can be found in the U.S. patents cited above with reference to the description of the substantially aliphatic polymer (A). These same patents are hereby incorporated by reference for their teachings with regard to reaction pressures, solvents, etc.

The recovery of the substituted acids produced by the process of this invention can be accomplished by means well known to those of skill in the art, such as distillation, crystallization, precipitation, dialysis, absorption, etc. Often, however, it is not necessary to recover the product if it is to be used as an intermediate (e.g., acylating agent) for the formation of other additive products.

In certain instances, it may also be desirable to convert the nature of the product from, for example, the anhydride to a free acid form. Techniques for carrying out these various conversions are well known to those of skill in the art of producing lubricant and fuel additives and need not be explained in detail here.

The following are specific illustrative examples of the improved process of the invention and include the best modes of the invention presently known. In these examples, as well as in other parts in the specification and the appended claims, all percentages and parts are by weight, and all temperatures are in degrees centigrade unless otherwise stated expressly to the contrary.

EXAMPLE A

A mixture of 3101 parts (3.5 equivalents) of polyisobutene (Mn-886) and 347 parts of maleic anhydride (3.54 equivalents) is prepared in a reaction flask equipped with stirrer, thermometer, sub-surface chlorine gas inlet and heated air condenser. The mixture is heated to a temperature of about 110° C. whereupon 26 parts (0.37 equivalent) of chlorine gas is added to the reaction vessel as the temperature of the mixture is raised from 110° C to about 190° C. The chlorine was added continuously over a period of four hours.

The reaction vessel then is modified to allow for a positive nitrogen blanket, and the temperature of the mixture is raised to 215° C. until a net saponification number of about 80 is reached.

Chlorine gas (82 parts, 1.15 equivalents) is added to the reaction flask continuously over a period of four hours while maintaining the reaction temperature of between about 180° to 225° C. Heating of the reaction mixture is continued until no additional hydrogen chloride is evolved. At the end of the heating period, nitrogen is blown through the reaction mixture at 190° C. to remove volatile material. The residue is the desired product obtained in 97% yield, and the product is found to have a saponification number (according to ASTM procedure D-94 ) of about 100.

EXAMPLE B

A three-liter flask equipped with a stirrer, thermowell, chlorine inlet, heated air condenser and dry Friedrich condenser is charged with 1,502 parts (1.66 equivalents) of polyisobutylene having a number average molecular weight of 905 and 155 (1.58 equivalents) parts of maleic anhydride. The materials are heated to 100° at which time stirring is begun. The mixture is heated to 190° over a period of four hours while 9 parts of chlorine is added at a uniform rate. Chlorine addition is discontinued and replaced with a very low rate of nitrogen blowing. The materials are heated to 210° and held at 210° for 19.5 hours. A sample of the reaction product is taken after 18 hours of heating and stripped. The stripped sample has a total acid number of 67. The chlorine feed is then resumed, and 60 grams chlorine is added at four hours at 210° C. The reaction mixture is then heated for 16 hours at 190° and stripped to 190° at 0.02 millimeters mercury for one hour. The residue is the desired product.

EXAMPLE C

To a reactor as described in Example A, there is charged 2984 parts polyisobutylene having a number average molecular weight of 915 and 331 parts maleic anhydride. The mixture is heated to 110° whereupon stirring and chlorine addition is begun. The reaction mixture is heated from 110° to 190° over four hours while 28 parts chlorine gas is added uniformly. Chlorine addition is discontinued and a nitrogen purge is begun. The reaction is heated to 200° over 1.5 hours and held at 200° for two additional hours, heated to 207° and held at 207° for 16.5 hours. The total acid number equals 80. Chlorine addition is resumed and 81 parts chlorine is added at 207° over 4.5 hours. The materials are nitrogen blown at 190° for 17 hours and then stripped to 190° at 0.9 millimeters mercury for one hour. The clear liquid residue is the product having a saponification number of about 100.

EXAMPLE D

To a reactor as described in Example B, there is charged 3097 parts polyisobutylene having a number average molecular weight of 911, and 33 parts maleic anhydride. The mixture is heated to 110° whereupon 35 parts chlorine gas are added over four hours while the temperature is increased from 110° to 190°. The temperature is increased to 215° while nitrogen blowing. Additional maleic anhydride (339 parts) is added in increments over two hours while the temperature is maintained at 205°-215°. The mixture is heated at 188°-210° under a nitrogen blanket for 16 hours. A stripped sample of material at this point of the reaction has a total acid number of 72.9. The reaction mixture is heated to 210° and held at 210° for seven hours. A stripped sample has an acid number of 81.3. Chlorine (81 parts) is added over 4.5 hours at 190°-210°. The reaction mixture is blown with a nitrogen at 210° for 16 hours. The material is then stripped to 210° at 5 millimeters mercury over one hour. The clear liquid residue is the product having a saponification number of about 102.

EXAMPLE E

To a reactor equipped with a stirrer, reflux column, condenser and receiver is charged 1000 parts of a polyisobutylene having a number average molecular weight of 950. The materials are heated to 77° C. and 105 parts maleic anhydride is added. The temperature is increased to 110° over three hours, and 3.5 parts chlorine gas is added over two hours while heating the reaction mixture to 125°. The batch is heated under a nitrogen purge to 211° in 11 hours whereupon 22.6 parts additional maleic anhydride is added in three increments during the heating period to maintain a total acid number of 105. The batch is held at 215° for 6.5 hours. Chlorine addition is resumed and 18 parts chlorine gas is added over 3.5 hours at 210°. The batch is blown with nitrogen via a submerged line for 3.5 hours to remove excess maleic anhydride. The residue is the desired product.

The substituted carboxylic compounds of this invention have utility, in and of themselves, as additives for lubricant and fuel compositions in the same manner as the known high molecular weight carboxylic acid acylating agents of the prior art. For example, the compounds of this invention which are succinic acids, succinic acid anhydrides, or lower alkyl esters of succinic acids can be used as fuel additives to reduce deposit formations. U.S. Pat. No. 3,346,354 is expressly incorporated herein by reference for instructions for using the known high molecular weight carboxylic acid acylating agents since those instructions are applicable to the substituted carboxylic acids and derivatives thereof of this invention. Similarly, U.S. Pat. No. 3,288,714 is expressly incorporated herein by reference for its teachings of how to use known high molecular weight carboxylic acid acylating agents which are succinic anhydrides as additives in lubricant compositions where they function as dispersant/detergents since these teachings are applicable to the acids and derivatives of this invention.

For the same reason, U.S. Pat. No. 3,714,042 is expressly incorporated hereby by reference for its teachings with respect to how to use the acids and derivatives of this invention to treat overbased complexes. The carboxylic acids and derivatives of this invention containing succinic acid groups, succinic anhydride groups, and succinic ester groups can be used to treat basic metal sulfonate complexes, sulfonate-carboxylate complexes, and carboxylate complexes in the same manner and according to the same procedure as described in U.S. Pat. No. 3,714,042 by replacing the high molecular weight carboxylic acid acylating agents discussed therein with the acylating reagents of this invention on an equivalent weight basis.

Because the substituted carboxylic acids and derivatives thereof of this invention have utility in and of themselves, beyond that of being intermediates for preparing other novel compositions, lubricant compositions and concentrates containing these compounds, as mentioned hereinbefore, and described more fully hereafter constitute a part of this invention. For brevity, the substituted carboxylic acids, anhydrides, esters and other derivatives of this invention, will be referred to herein generally as acylating reagents.

Nevertheless, the principal use of the acylating reagents of this invention is as intermediates in processes for preparing carboxylic derivative compositions comprising reacting one or more of the acylating reagents prepared in accordance with the improved method of this invention with a reactant selected from the group consisting of (a) amines characterized by the presence within their structure of at least one H-N< group, (b) alcohols, (c) reactive metal or reactive metal compounds, and (d) a combination of two or more of (a) through (c), the components of (d) being reacted with said acylating reagents simultaneously or sequentially in any order.

The amines, (that is, reactant (a) above) characterized by the presence within their structure of at least one H-N< group can be monoamines or polyamines. For purposes of this invention, hydrazine and substituted hydrazines containing up to three substituents are included as amines suitable for preparing carboxylic derivative compositions. Mixtures of two or more amines can be used in the reaction with one or more acylating reagents of this invention. Preferably, the amine contains at least one primary amino group (i.e., —NH$_2$) and more preferably the amine is a polyamine, especially a polyamine containing at least two H—N< groups, either or both of which are primary or secondary amines. The polyamines not only result in carboxylic acid derivative compositions which are usually more effective as dispersant/detergent additives, relative to derivative compositions derived from monoamines, but these preferred polyamines result in carboxylic derivative compositions which exhibit more pronounced V.I. improving properties. Monoamines, and polyamines suitable as reactant (a) are described in greater detail hereinafter.

Alcohols which can be used as reactant (b) include the monohydric and polyhydric alcohols. Again the polyhydric alcohols are preferred since they usually result in carboxylic derivative compositions which are more effective dispersant/detergents relative to carboxylic derivative compositions derived from monohydric alcohols. Further, the carboxylic acid derivative compositions derived from polyhydric alcohols exhibit very pronounced V.I. improving properties and are especially preferred reactants. Alcohols suitable for use as reactant (b) are described in greater detail hereinafter.

Reactive metals and reactive metal compounds useful as reactant (c) are those which are known to form salts and complexes when reacted with carboxylic acid and carboxylic acid acylating agents. These metals and metal compounds are described further hereinafter.

The monoamines and polyamines useful as reactant (a) must contain at least one H—N< group. Therefore, they have at least one primary amino (i.e., $H_2N$—) or secondary amino (i.e., H—N<) group. The amines can be aliphatic, cycloaliphatic, aromatic, or heterocyclic, including aliphatic-substituted cycloaliphatic, aliphatic-substituted aromatic, aliphatic-substituted heterocyclic. cycloaliphatic-substituted aliphatic, cycloaliphatic-substituted aromatic cycloaliphatic-substituted heterocyclic, aromatic-substituted aliphatic, aromatic-substituted cycloaliphatic, aromatic-substituted heterocyclic, hetero-cyclic-substituted aliphatic, heterocyclic-substituted alicyclic, and heterocyclic-substituted aromatic amines and may be saturated or unsaturated. If unsaturated, the amine will be free from acetylenic unsaturation. The amines may also contain non-hydrocarbon substituents or groups as long as these groups do not significantly interfere with the reaction of the amines with the acylating reagents of this invention. Such non-hydrocarbon substituents or groups include lower alkoxy, lower alkyl mercapto, nitro, interrupting groups such as —O— and —S— (e.g., as in such groups as —$CH_2CH_2$—X—$CH_2CH_2$— where X is —O— or —S—).

With the exception of the branched polyalkylene polyamine, the polyoxyalkylene polyamines, and the high molecular weight hydrocarbyl-substituted amines described more fully hereafter, the amines used as (a) ordinarily contain less than about 40 carbon atoms in total and usually not more than about 20 carbon atoms in total.

Aliphatic monoamines include mono-aliphatic and di-aliphatic substituted amines wherein the aliphatic groups can be saturated or unsaturated and straight or branched chain. Thus, they are primary or secondary aliphatic amines. Such axines include, for example, mono- and dialkyl-substituted amines, mono- and dialkenyl-substituted amines, and amines having one N-alkenyl substituent and one N-alkyl substituent and the like. The total number of carbon atoms in these aliphatic monoamines will, as mentioned before, normally not exceed about 40 and usually not exceed about 20 carbon atoms. Specific examples of such monoamines include ethylamine, diethylamine, n-butylamine, di-n-butylamine, allylamine, isobutylamine, cocoamine, stearylamine, laurylamine, methyllaurylamine, oleylamine, N-methyl-octylamine, dodecylamine, octadecylamine, and the like. Examples of cycloaliphatic-substituted aliphatic amines, aromatic-substituted aliphatic amines, and heterocyclic-substituted aliphatic amines, include 2-(cyclohexyl)-ethylamine, benzylamine, phenethylamine, and 3-(furylpropyl)amine.

Cycloaliphatic monoamines are those monoamines wherein there is one cycloaliphatic substituent attached directly to the amino nitrogen through a carbon atom in the cyclic ring structure. Examples of cycloaliphatic monoamines include cyclohexylamines, cyclopentylamines, cyclohexenylamines, cyclopentenylamines, N-ethyl-cyclohexylamine, dicyclohexylamines, and the like. Examples of aliphatic-substituted, aromatic-substituted, and heterocyclic-substituted cycloaliphatic monoamines include propyl-substituted cyclohexylamines, phenyl-substituted cyclopentylamines, and pyranyl-substituted cyclohexylamine.

Aromatic amines suitable as (a) include those monoamines wherein a carbon atom of the aromatic ring structure is attached directly to the amino nitrogen. The aromatic ring will usually be a mononuclear aromatic ring (i.e., one derived from benzene) but can include fused aromatic rings, especially those derived from naphthalene. Examples of aromatic monoamines include aniline, di(para-methylphenyl)-amine, naphthylamine, N-(n-butyl)aniline, and the like. Examples of aliphatic-substituted, cycloaliphatic-substituted, and heterocyclic-substituted aromatic monoamines are para-ethoxyaniline, para-dodecylaniline, cyclohexyl-substituted naphthylamine, and thienyl-substituted aniline.

Polyamines suitable as (a) are aliphatic. cycloaliphatic and aromatic polyamines analogous to the above-described monoamines except for the presence within their structure of at least one other amino nitrogen. The other amino nitrogen can be a primary, secondary or tertiary amino nitrogen. Examples of such polyamines include N-amino-propyl-cyclohexylamines, N-N'-di-n-butyl-para-phenylene diamine, bis-(paraaminophenyl)methane, 1,4-diaminocyclohexane, and the like.

Heterocyclic mono- and polyamines can also be used as (a) in making the carboxylic derivative compositions of this invention. As used herein, the terminology "heterocyclic mono- and polyamine(s)" is intended to describe those heterocyclic amines containing at least one primary or secondary amino group and at least one nitrogen as a heteroatom in the heterocyclic ring. However, as long as there is present in the heterocyclic mono- and polyamines at least one primary or secondary amino group, the hetero-N atom in the ring can be a tertiary amino nitrogen; that is, one that does not have hydrogen attached directly to the ring nitrogen. Heterocyclic amines can be saturated or unsaturated and can contain various substituents such as nitro, alkoxy, alkyl mercapto, alkyl, alkenyl, aryl, alkaryl, or aralkyl substituents. Generally, the total number of carbon atoms in the substituents will not exceed about 20. Heterocyclic amines can contain hetero atoms other than nitrogen, especially oxygen and sulfur. Obviously they can contain more than one nitrogen hetero atom. The 5- and 6-membered heterocyclic rings are preferred.

Among the suitable heterocyclics are aziridines, azetidines, azolidines, tetra- and di-hydro pyridines, pyrroles, indoles, piperidines, imidazoles, di- and tetra-hydroimidazoles, piperazines, isoindoles, purines, morpholines, thiomorpholines. N-aminoalkylmorpholines. N-aminoalkylthiomorpholines. N-aminoalkylpiperazines, N,N'-di-aminoalkylpiperazines, azepines, azocines, azonines, azecines and tetra-, di- and perhydro derivatives of each of the above and mixtures of two or more of these heterocyclic amines. Preferred heterocyclic amines are the saturated 5- and 6-membered heterocyclic amines containing only nitrogen, oxygen and/or sulfur in the hetero ring, especially the piperidines, piperazines, thiomorpholines, morpholines, pyrrolidines, and the like. Piperidines, aminoalkyl-substituted piperidines, piperazine, aminoalkyl-substituted piperazines, morpholine, aminoalkyl-substituted piperazines, morpholine, aminoalkyl-substituted morpholines, pyrrolidine, and aminoalkyl-substituted pyrrolidines, are especially preferred. Usually the aminoalkyl substituents are substituted on a nitrogen atom forming part of the hetero ring. Specific examples of such heterocyclic amines include N-aminopropylmorpholine, N-aminoethylpiperazine, and N,N'-di-aminoethylpiperazine.

Hydroxyamines both mono- and polyamines, analogous to those described above are also useful as (a) provided they contain at least one primary or secondary amino group. Hydroxy-substituted amines having only tertiary amino nitrogen such as in tri-hydroxyethyl amine, are thus excluded as (a) (but can be used as (b) as disclosed hereafter). The hydroxy-substituted amines contemplated are those having hydroxy substituents bonded directly to a carbon atom other than a carbonyl carbon atom; that is, they have hydroxy groups capable of functioning as alcohols. Examples of such hydroxy-substituted amines include ethanolamine, di-(3-hydroxypropyl)-amine, 3-hydroxybutyl-amine, 4-hydroxybutyl-amine, diethanolamine, di-(2-hydroxypropyl)-amine, N-(hydroxypropyl) propylamine, N-(2-hydroxyethyl)-cyclohexylamine, 3-hydroxycyclopentylamine, para-hydroxyaniline, N-hydroxyethyl piperazine, and the like.

Also suitable as amines are the aminosulfonic acids and derivatives thereof corresponding to the general formula:

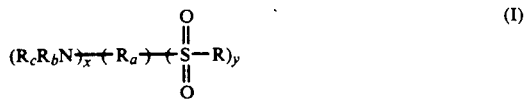

wherein R is —OH, —NH$_2$, etc., $R_a$ is a polyvalent organic radical having a valence equal to +y; $R_b$ and $R_c$ are each independently hydrogen, hydrocarbyl, and substituted hydrocarbyl with the proviso that at least one of $R_b$ or $R_c$ is hydrogen per aminosulfonic acid molecule; x and y are each integers equal to or greater than one. From the formula, it is apparent that each amino sulfonic reactant is characterized by at least one HN< or H$_2$N— group and at least one

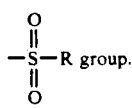

These sulfonic acids can be aliphatic. cycloaliphatic, or aromatic aminosulfonic acids and the corresponding functional derivatives of the sulfo group. Specifically, the aminosulfonic acids can be aromatic aminosulfonic acids, that is, where $R_a$ is a polyvalent aromatic radical such as phenylene where at least one

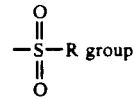

is attached directly to a nuclear carbon atom of the aromatic radical. The aminosulfonic acid may also be a mono-amino aliphatic sulfonic acid; that is, an acid where x is one and $R_a$ is a polyvalent aliphatic radical such as ethylene, propylene, trimethylene, and 2-methylene propylene. Suitable aminosulfonic acids and derivatives thereof useful as reactant (a) are disclosed in U.S. Pat. Nos. 3,029,250; 3,367,864; and 3,926,820: which are expressly incorporated herein by reference for such disclosure.

Hydrazine and substituted-hydrazine can also be used as (a). At least one of the nitrogens in the hydrazine used as (a) must contain a hydrogen directly bonded thereto. Preferably there are at least two hydrogens bonded directly to hydrazine nitrogen and, more preferably, both hydrogens are on the same nitrogen. The substituents which may be present on the hydrazine include alkyl, alkenyl, aryl, aralkyl, alkaryl, and the like. Usually, the substituents are alkyl, especially lower alkyl, phenyl, and substituted phenyl such as lower alkoxy substituted phenyl or lower alkyl substituted phenyl. Specific examples of substituted hydrazines are methylhydrazine, N,N'-dimethylhydrazine, phenylhydrazine, N-phenyl-N'-ethyl-hydrazine, N-(para-tolyl)-N'-(n-butyl)-hydrazine, N,N'-di-(para-chlorophenyl)-hydrazine and N-phenyl-N'-cyclohexyl-hydrazine.

The high molecular weight hydrocarbyl amines, both monoamines and polyamines, which can be used as (a) are generally prepared by reacting a chlorinated polyolefin having a molecular weight of at least about 400 with ammonia or amine. Such amines are known in the art and described, for example, in U.S. Pat. Nos. 3,275,554 and 3,438,757, both of which are expressly incorporated herein by reference for their disclosure in regard to how to prepare these amines. All that is required for use of these amines as (a) is that they possess at least one primary or secondary amino group.

Another group of amines suitable for use as (a) are branched polyalkylene polyamines. The branched polyalkylene polyamines are polyalkylene polyamines wherein the branched group is a side chain containing on the average at least one nitrogen-bonded aminoalkylene

group per nine amino units present on the main chain for example, 1-4 of such branched chains per nine units on the main chain, but preferably one side chain unit per nine main chain units. Thus, these polyamines contain at least three primary amino groups and at least one tertiary amino group.

These reagents may be expressed by the formula:

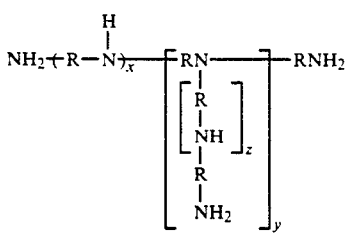 (III)

wherein R is an alkylene group such as ethylene, propylene, butylene and other homologues (both straight chained and branched), etc., but preferably ethylene; and x, y and z are integers, x being for example, from 4 to 24 or more but preferably 6 to 18, y being for example 1 to 6 or more but preferably 1 to 3, and z being for example 0 to 6 but preferably 0 to 1. The x and y units may be sequential, alternative, orderly or randomly distributed.

A preferred class of such polyamines includes those of the formula

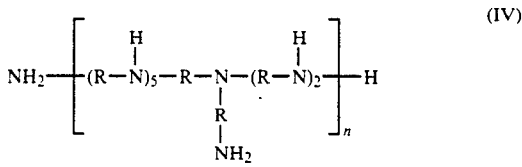 (IV)

wherein n is an integer, for example, 1-20 or more but preferably 1-3, wherein R is preferably ethylene, but may be propylene, butylene, etc. (straight chained or branched).

U.S. Pat. Nos. 3,200,106 and 3,259,578 are expressly incorporated herein by reference for their disclosure of how to make such polyamines and processes for reacting them with carboxylic acid acylating agents since analogous processes can be used with the acylating reagents of this invention.

Suitable amines also include polyoxyalkylene polyamines, e.g., polyoxyalkylene diamines and polyoxyalkylene triamines, having average molecular weights ranging from about 200 to 4000 and preferably from about 400 to 2000. Illustrative examples of these polyoxyalkylene polyamines may be characterized by the formula:

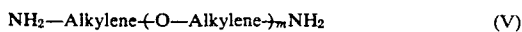 (V)

wherein m has a value of about 3 to 70 and preferably about 10 to 35.

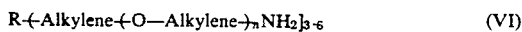 (VI)

wherein n is such that the total value is from about 1 to 40 with the proviso that the sum of all of the n's is from about 3 to about 70 and generally from about 6 to about 35 and R is a polyvalent saturated hydrocarbon radical of up to 10 carbon atoms having a valence of 3 to 6. The alkylene groups may be straight or branched chains and contain from 1 to 7 carbon atoms, and usually from 1 to 4 carbon atoms. The various alkylene groups present within Formulae V and VI may be the same or different.

The preferred polyoxyalkylene polyamines for purposes of this invention include the polyoxyethylene and polyoxypropylene diamines and the polyoxypropylene triamines having average molecular weights ranging from about 200 to 2000. The polyoxyalkylene polyamines are commercially available and may be obtained for example, from the Jefferson Chemical Company, Inc. under the trade name "Jeffamines D-230, D 400, D 1000, D-2000, T-403, etc.".

U.S. Pat. Nos. 3,804,763 and 3,948,800 are expressly incorporated herein by reference for their disclosure of such polyoxyalkylene polyamines and process for acylating them with carboxylic acid acylating agents which processes can be applied to their reaction with the acylating reagents of this invention.

The most preferred amines for use as (a) are the alkylene polyamines, including the polyalkylene polyamines, as described in more detail hereafter. The alkylene polyamines include those conforming to the formula

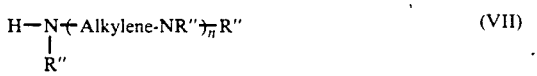 (VII)

wherein n is from 1 to about 10; each R' is independently a hydrogen atom, a hydrocarbyl group or a hydroxy-substituted hydrocarbyl group having up to about 30 atoms, and the "Alkylene" group has from about 1 to about 10 carbon atoms, but the preferred alkylene is ethylene or propylene. Especially preferred are the alkylene polyamines where each R" is hydrogen with the ethylene polyamines and mixtures of ethylene polyamines being the most preferred. Usually n will have an average value of from about 2 to about 7. Such alkylene polyamines include methylene polyamine. ethylene polyamines, butylene polyamines, propylene polyamines, pentylene polyamines, hexylene polyamines, heptylene polyamines, etc. The higher homologs of such amines and related aminoalkyl-substituted piperazines are also included.

Alkylene polyamines useful in preparing the carboxylic derivative compositions include ethylene diamine, triethylene tetramine, propylene diamine, trimethylene diamine, hexamethylene diamine decamethylene diamine, octamethylene diamine, di(heptamethylene)triamine, tripropylene tetramine, tetraethylene pentamine, trimethylene diamine, pentaethylene hexamine, di(trimethylene)triamine, N-(2-aminoethyl)piperazine, 1,4-bis(2-aminoethyl)piperazine, and the like. Higher homologs as are obtained by condensing two or more of the above-illustrated alkylene amines are useful as reactant (a) as are mixtures of two or more of any of the aforedescribed polyamines.

Ethylene polyamines, such as those mentioned above, are especially useful for reasons of cost and effectiveness. Such polyamines are described in detail under the heading "Diamines and Higher Amines" in The Encyclopedia of Chemical Technology. Second Edition, Kirk and Othmer, Volume 7, pages 27-39, Interscience publishers, Division of John Wiley and Sons, 1965, which is hereby incorporated by reference for their disclosure of useful polyamines. Such compounds are prepared most conveniently by the reaction of an alkylene chloride with ammonia or by reaction of an ethylene imine with a ring-opening reagent such as ammonia, etc. These reactions result in the production of the somewhat complex mixtures of alkylene polyamines, including cyclic condensation products such as piperazines. The mixtures are particularly useful in preparing novel sulfur-containing compositions of matter of this invention. On the other hand, quite satisfactory products can also be obtained by the use of pure alkylene polyamines.

Other useful types of polyamine mixtures are those resulting from stripping of the above-described polyamine mixtures. In this instance, lower molecular weight polyamines and volatile contaminants are removed from an alkylene polyamine mixture to leave as residue what is often termed "polyamine bottoms". In general, alkylene polyamine bottoms can be characterized as having less than two, usually less than 1% by weight material boiling below about 200° C. In the instance of ethylene polyamine bottoms, which are readily available and found to be quite useful, the bottoms contain less than about 2% by weight total diethylene triamine (DETA) or triethylene tetramine (TETA). A typical sample of such ethylene polyamine bottoms obtained from the Dow Chemical Company of Freeport, Texas designated "E-100" showed a specific gravity at 15.6° C of 1.0168. a percent nitrogen by weight of 33.15 and a viscosity at 40° C. of 121 centistokes. Gas chromatography analysis of such a sample showed it to contain about 0.93% "Light Ends" (DETA? ), 0.72% TETA, 21.74% tetraethylene pentamine and 76.61% pentaethylene hexamine and higher (by weight). These alkylene polyamine bottoms include cyclic condensation products such as piperazine and higher analogs of diethylene triamine, triethylene tetramine and the like.

When reacted with the aforedescribed acylating agents, these polyamine bottoms often provide carboxylic derivative compositions which impart improved viscosity index properties to lubricants containing them.

These alkylene polyamine bottoms can be reacted by themselves with the acylating agent, in which case the amino reactant consists essentially of alkylene polyamine bottoms, or they can be used with other amines and polyamines, or alcohols or mixtures thereof. In these latter cases at least one amino reactant comprises alkylene polyamine bottoms.

Hydroxyalkyl alkylene polyamines having one or more hydroxyalkyl substituents on the nitrogen atoms, are also useful in preparing amide or ester functional derivatives of the afore-described olefinic carboxylic acids. Preferred hydroxyalkyl-substituted alkylene polyamines are those in which the hydroxyalkyl group is a lower hydroxyalkyl group, i.e., having less than 8 carbon atoms. Examples of such hydroxyalkyl-substituted polyamines include N-(2-hydroxy-ethyl)ethylene diamine, N,N-bis(2-hydroxyethyl)ethylene diamine, 1-(2hydroxyethyl)piperazine, monohydroxypropyl-substituted diethylene triamine, dihydroxypropyl-substituted tetraethylene pentamine, N-(3-hydroxybutyl)tetramethylene diamine, etc. Higher homologs as are obtained by condensation of the above-illustrated hydroxy alkylene polyamines through amino radicals or through hydroxy radicals are likewise useful as (a). Condensation through amino radicals results in a higher amine accompanied by removal of ammonia and condensation through the hydroxy radicals results in products containing ether linkages accompanied by removal of water.

The carboxylic derivative compositions produced from the acylating reagents of this invention and the amines described hereinbefore produce acylated amines which include amine salts, amides, imides and imidazolines as well as mixtures thereof. To prepare carboxylic acid derivatives from the acylating reagents and the amines, one or more acylating reagents and one or more amines are heated, optionally in the presence of a normally liquid, substantially inert organic liquid solvent/diluent, at temperatures in the range of about 80° C. up to the decomposition point (where the decomposition point is as previously defined) but normally at temperatures in the range of about 100° C. up to about 300° C. provided 300° C. does not exceed the decomposition point. Temperatures of about 125° C. to about 250° C. are normally used. The acylating reagent and the amine are reacted in amounts sufficient to provide from about one-half equivalent to about 2 moles of amine per equivalent of acylating reagent. For purposes of this invention, an equivalent of amine is that amount of the amine corresponding to the total weight of amine divided by the total number of nitrogens present. Thus, octylamine has an equivalent weight equal to its molecular weight; ethylene diamine has an equivalent weight equal to one-half its molecular weight; and aminoethylpiperazine has an equivalent weight equal to one-third its molecular weight.

The numbers of equivalents of acylating reagent depends on he number of carboxylic functions

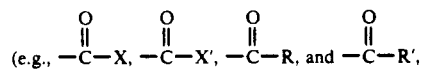

wherein X, X', R and R' are as defined above) present in the acylating reagent. Thus, the number of equivalents of acylating reagents will vary with the number of succinic groups present therein. In determining the number of equivalents of acylating reagents, those carboxyl functions which are not capable of reacting as a carboxylic acid acylating agent are excluded. In general, however, there are two equivalents of acylating reagent for each succinic group in the acylating reagents or, from another viewpoint, two equivalents for each group in the acylating reagents derived from (B); i.e., the acidic reactant from which the acylating reagent is prepared. Conventional techniques are readily available for determining the number of carboxyl functions (e.g., acid number, saponification number) and, thus, the number of equivalents of acylating reagent available to react with amine.

Because the acylating reagents of this invention can be used in the same manner as the high molecular weight acylating agents of the prior art in preparing acylated amines suitable as additives for lubricating oil compositions, U.S. Pat. Nos. 3,172,892; 3,219,666; and 3,272,746 are expressly incorporated herein by reference for their disclosure with respect to the procedures applicable to reacting the acylating reagents of this invention with the amines as described above. In applying the disclosures of these patents to the acylating reagents of this invention, the acylating reagents of this invention can be substituted for the high molecular weight carboxylic acid acylating agents disclosed in these patents on an equivalent basis. That is, where one equivalent of the high molecular weight carboxylic acylating agent disclosed in these incorporated patents is utilized, one equivalent of the acylating reagent of this invention can be used. These patents are also incorporated by reference for their disclosure of how to use the acylated amines thus produced as additives in lubricating oil compositions. Dispersant/detergent properties can be imparted to lubricating oils by incorporating the acylated amines produced by reacting the acylating reagents of this invention with the amines described above on an equal weight basis with the acylated amines disclosed in these patents. In fact, equivalent or better dispersant/detergent results can normally be achieved with lesser amounts of the product of the acylating reagents of this invention and amines.

Alcohols useful as (b) in preparing carboxylic derivative compositions of this invention from the acylating reagents previously described include those compounds of the general formula $$R_3(OH)_m \quad \text{(VIII)}$$

wherein $R_3$ is a monovalent or polyvalent organic radical joined to the —OH groups through carbon-to-oxygen bonds (that is, —COH wherein the carbon is not part of a carbonyl group) and m is an integer of from 1 to about 10, usually 2 to about 6. As with the amine reactant (a), the alcohols can be aliphatic, cycloaliphatic, aromatic, and heterocyclic, including aliphatic-substituted cycloaliphatic alcohols, aliphatic-substituted aromatic alcohols, aliphatic-substituted heterocyclic alcohols, cycloaliphatic-substituted aliphatic alcohols, cycloaliphatic-substituted aromatic alcohols, cycloaliphatic-substituted heterocyclic alcohols, heterocyclic-substituted aliphatic alcohols, heterocyclic-substituted cycloaliphatic alcohols, and heterocyclic-substituted aromatic alcohols. Except for the polyoxyalkylene alcohols, the mono- and polyhydric alcohols corresponding to Formula VIII will usually contain not more than about 40 carbon atoms and generally not more than about 20 carbon atoms. The alcohols may contain non-hydrocarbon substituents of the same type mentioned with respect to the amines above, that is, non-hydrocarbon substituents which do not interfere with the reaction of the alcohols with the acylating reagents of this invention. In general, polyhydric alcohols are preferred. Combinations of amines and polyhydric alcohols result in carboxylic derivative compositions which have exceptional V.I. improving qualities.

Among the polyoxyalkylene alcohols suitable as reactant (b) in the preparation of the carboxylic derivative compositions of this invention are the polyoxyalkylene alcohol demulsifiers for aqueous emulsions. The terminology "demulsifier for aqueous emulsions" as used in the present specification and claims is intended to describe those polyoxyalkylene alcohols which are capable of preventing or retarding the formation of aqueous emulsions or "breaking" aqueous emulsions. The terminology "aqueous emulsion" is generic to oil-in-water and water-in-oil emulsions.

Many commercially available polyoxyalkylene alcohol demulsifiers can be used as reactant (b). Useful demulsifiers are the reaction products of various organic amines, carboxylic acid amides, and quaternary ammonium salts with ethyleneoxide. Such polyoxyethylated amines, amides, and quaternary salts are available from Armour Industrial Chemical Co. under the names ETHODUOMEEN T, an ethyleneoxide condensation product of an N-alkyl alkylenediamine under the name DUOMEEN T; ETHOMEENS, tertiary amines which are ethyleneoxide condensation products of primary fatty amines; ETHOMIDS, ethyleneoxide condensates of fatty acid amides; and ETHOQUADS, polyoxyethylated quaternary ammonium salts such as quaternary ammonium chlorides.

The preferred demulsifiers are liquid polyoxyalkylene alcohols and derivatives thereof. The derivatives contemplated are the hydrocarbyl ethers and the carboxylic acid esters obtained by reacting the alcohols with various carboxylic acids. Illustrative hydrocarbyl groups are alkyl, cycloalkyl, alkylaryl, aralkyl, alkylaryl alkyl, etc., containing up to about 40 carbon atoms. Specific hydrocarbyl groups are methyl, butyl, dodecyl, tolyl, phenyl, naphthyl, dodecylphenyl, p-octylphenyl ethyl, cyclohexyl, and the like. Carboxylic acids useful in preparing the ester derivatives are mono- or polycarboxylic acids such as acetic acid, valeric acid, lauric acid, stearic acid, succinic acid, and alkyl or alkenyl-substituted succinic acids wherein the alkyl or alkenyl group contains up to about 20 carbon atoms. Members of this class of alcohols are commercially available from various sources; e.g., PLURONIC polyols from Wyandotte Chemicals Corporation; POLYGLYCOL 112-2, a liquid triol derived from ethyleneoxide and propyleneoxide available from Dow Chemical Co.; and TERGITOLS, dodecylphenyl or nonylphenyl polyethylene glycol ethers, and UCONS. polyalkylene glycols and various derivatives thereof, both available from Union Carbide Corporation. However, the demulsifiers used as reactant (b) must have an average of at least one free alcoholic hydroxyl group per molecule of polyoxyalkylene alcohol. For purposes of describing these polyoxyalkylene alcohols which are demulsifiers, an alcoholic hydroxyl group is one attached to a carbon atom that does not form part of an aromatic nucleus.

In this class of preferred polyoxyalkylene alcohols are those polyols prepared as "block" copolymers. Thus, a hydroxy-substituted compound. $R_4$—$(OH)_q$ (wherein q is 1 to 6, preferably 2 to 3, and $R_4$ is the residue of a mono- or polyhydric alcohol or mono- or polyhydroxy phenol, naphthol, etc.) is reacted with an alkylene oxide,

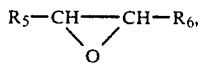

to form a hydrophobic base, $R_5$ being a lower alkyl group of up to 4 carbon atoms, $R_6$ being H or the same as $R_5$ with the proviso that the alkylene oxide does not contain in excess of 10 carbon atoms. This base is then reacted with ethylene oxide to provide a hydrophylic portion resulting in a molecule having both hydrophobic and hydrophylic portions. The relative sizes of these portions can be adjusted by regulating the ratio of reactants, time of reaction, etc., as is obvious to those skilled in the art. It is within the skill of the art to prepare such polyols whose molecules are characterized by hydrophobic and hydrophylic moieties present in a ratio rendering them suitable as demulsifiers for aqueous emulsions in various lubricant compositions and thus suitable as reactant (b). Thus, if more oil-solubility is needed in a given lubricant composition, the hydrophobic portion can be increased and/or hydrophylic portion decreased. If greater aqueous emulsion breaking capability is required, the hydrophylic and/or hydrophobic portions can be adjusted to accomplish this.

Compounds illustrative of $R_4(OH)_q$ include aliphatic polyols such as the alkylene glycols and alkane polyols, e.g., ethylene glycol, propylene glycol, trimethylene glycol, glycerol, pentaerythritol, erythritol, sorbitol, mannitol, and the like and aromatic hydroxy compounds such as alkylated mono- and polyhydric phenols and naphthols, e.g., cresols, heptylphenols, dodecylphenols, dioctylphenols, triheptylphenols, resorcinol, pyrogallol, etc.

Polyoxyalkylene polyol demulsifiers which have two or three hydroxyl groups and molecules consisting essentially of hydrophobic portions comprising

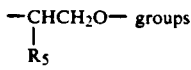

wherein $R_5$ is lower alkyl of up to three carbon atoms and hydrophylic portions comprising —CH$_2$CH$_2$O— groups are particularly preferred as reactant (b). Such polyols can be prepared by first reacting a compound of the formula $R_4$ (OH)$_q$ where q is 2–3 with a terminal alkylene oxide of the formula

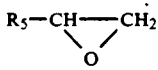

and then reacting that product with ethylene oxide. $R_4$ (OH)$_q$ can be, for example, TMP (trimethylolpropane). TME (trimethylolethane), ethylene glycol, trimethylene glycol, tetramethylene glycol, tri-(beta-hydroxypropyl)amine, 1,4-(2-hydroxyethyl)cyclohexane, N,N,N',N'-tetrakis(2-hydroxypropyl)ethylene diamine, N,N,N',N'-tetrakis(2-hydroxyethyl)ethylene diamine, naphthol, alkylated naphthol, resorcinol, or one of the other illustrative examples mentioned hereinbefore.

The polyoxyalkylene alcohol demulsifiers should have an average molecular weight of about 1000 to about 10,000, preferably about 2000 to about 7000. The ethyleneoxy groups (i.e.. —CH$_2$CH$_2$O—) normally will comprise from about 5% to about 40% of the total average molecular weight. Those polyoxyalkylene polyols where the ethyleneoxy groups comprise from about 10% to about 30% of the total average molecular weight are especially useful as (b). Polyoxyalkylene polyols having an average molecular weight of about 2500 to about 6000 where approximately 10%–20% by weight of the molecule is attributable to ethyleneoxy groups result in the formation of esters having particularly improved demulsifying properties. The ester and ether derivatives of these polyols are also useful as (b).

Representative of such polyoxyalkylene polyols are the liquid polyols available from Wyandotte Chemicals Company under the name PLURONIC Polyols and other similar polyols. These PLURONIC Polyols correspond to the formula

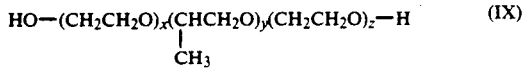

wherein x, y, and z are integers greater than 1 such that the —CH$_2$CH$_2$O— groups comprise from about 10% to about 15% by weight of the total molecular weight of the glycol, the average molecular weight of said polyols being from about 2500 to about 4500. This type of polyol can be prepared by reacting propylene glycol with propylene oxide and then with ethylene oxide.

Another group of polyoxyalkylene alcohol demulsifiers illustrative of the preferred glass discussed above are the commercially available liquid TETRONIC polyols sold by Wyandotte Chemicals Corporation. These polyols are represented by the general formula:

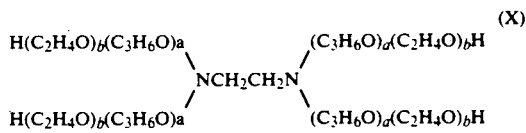

wherein a+b are integers wherein the overall molecular weight of the compound is over 1500, and the ethyleneoxy portion constitutes from 20% to 90% by weight of the molecule. Such polyols are described in U.S. Pat. No. 2,979,528 which is expressly incorporated herein by reference. Those polyols corresponding to the above formula having an average molecular weight of up to about 10,000 wherein the ethyleneoxy groups contribute to the total molecular weight in the percentage ranges discussed above are preferred. A specific example would be such a polyol having an average molecular weight of about 8000 wherein the ethyleneoxy groups account for 7.5%–12% by weight of the total molecular weight. Such polyols can be prepared by reacting an alkylene diamine such as ethylene diamine, propylene diamine, hexamethylene diamine, etc., with propylene oxide until the desired weight of the hydrophobic portion is reached. Then the resulting product is reacted with ethylene oxide to add the desired number of hydrophilic units to the molecules.

Another commercially available polyoxyalkylene polyol demulsifier falling within this preferred group is Dow Polyglycol 112-2, a triol having an average molecular weight of about 4000–5000 prepared from propylene oxides and ethylene oxides, the ethyleneoxy groups comprising about 18% by weight of the triol. Such triols can be prepared by first reacting glycerol, TME, TMP, etc., with propylene oxide to form a hydrophobic base and reacting that base with ethylene oxide to add hydrophilic portions.

Alcohols useful as reactant (b) also include alkylene glycols and polyoxyalkylene alcohols such as polyoxyethylene alcohols, polyoxypropylene alcohols, polyoxybutylene alcohols, and the like. These polyoxyalkylene alcohols (sometimes called polyglycols) can contain up to about 150 oxyalkylene groups wherein the alkylene radical contains from 2 to about 8 carbon atoms. Such polyoxyalkylene alcohols are generally dihydric alcohols. That is, each end of the molecule terminates with a —OH group. In order for such polyoxyalkylene alcohols to be useful as reactant (b), there must be at least one such —OH group. However, the remaining —OH group can be esterified with a monobasic, aliphatic or aromatic carboxylic acid of up to about 20 carbon atoms such as acetic acid, propionic acid, oleic acid, stearic acid, benzoic acid, and the like. The monoethers of these alkylene glycols and polyoxyalkylene glycols are also useful as reactant (b). These include the monoaryl ethers, monoalkyl ethers, and monoaralkyl ethers of these alkylene glycols and polyoxyalkylene glycols. This group of alcohols can be represented by the general formula

wherein $R_C$ is aryl such as phenyl, lower alkoxy phenyl, or lower alkyl phenyl; lower alkyl such as ethyl, propyl, tert-butyl, pentyl, etc.; and aralkyl such as benzyl, phenylethyl, phenylpropyl, p-ethylphenylethyl, etc.; p is zero to about 150, and $R_A$ and $R_B$ are lower alkylene of 2 up to about 8, preferably, 2 to 4 carbon atoms. Polyoxyalkylene glycols where the alkylene groups are ethylene or propylene and p is at least two as well as the monoethers thereof as described above are very useful.

The monohydric and polyhydric alcohols useful as reactant (b) include monohydroxy and polyhydroxy aromatic compounds. Monohydric and polyhydric phenols and naphthols are preferred hydroxyaromatic compounds. These hydroxy-substituted aromatic compounds may contain other substituents in addition to the hydroxy substituents such as halo, alkyl, alkenyl, alkoxy. alkylmercapto, nitro and the like. Usually, the hydroxy aromatic compound will contain 1 to 4 hydroxy groups. The aromatic hydroxy compounds are illustrated by the following specific examples: phenol, p-chlorophenol, p-nitrophenol, beta-naphthol, alpha-naphthol, cresols, resorcinol, catechol, thymol, eugenol, p,p'-dihydroxy-biphenyl, hydroquinone, pyrogallol, phloroglucinol, hexyl-resorcinol, orcinol, guaiacol, 2-chlorophenol, 2,4-dibutylphenol, propenetetramer-substituted phenol, didodecylphenol, alpha-decyl-betanaphthol, polyisobutenyl-(molecular weight of about 1000)-substituted phenol, the condensation product of heptylphenol with 0.5 moles of formaldehyde, the condensation product of octylphenol with acetone, di(hydroxyphenyl)oxide, di(hydroxyphenyl)sulfide, di-(hydroxyphenyl)ldisulfide, and 4-cyclohexylphenol. Phenol itself and aliphatic hydrocarbon-substituted phenols. e.g., alkylated phenols having up to 3 aliphatic hydrocarbon substituents are especially preferred. Each of the aliphatic hydrocarbon substituents may contain 100 or more carbon atoms but usually will have from 1 to 20 carbon atoms. Alkyl and alkenyl groups are the preferred aliphatic hydrocarbon substituents.

Further specific examples of monohydric alcohols which can be used as (b) include monohydric alcohols such as methanol, ethanol, isooctanol. dodecanol, cyclohexanol, cyclopentanol, biphenyl alcohol, hexatriacontanol, neopentyl alcohol, isobutyl alcohol, benzyl alcohol, beta-phenethyl alcohol. 2-methylcyclohexanol, beta-chloroethanol, monomethyl ether of ethylene glycol, monobutyl ether of ethylene glycol, monopropyl ether of diethylene glycol, monododecyl ether of triethylene glycol, monooleate of ethylene glycol, monostearate of diethylene glycol, sec-pentyl alcohol, tert-butyl alcohol, 5-bromododecanol, nitro-octadecanol, and dioleate of glycerol. Alcohols useful as reactant (b) may be unsaturated alcohols such as allyl alcohol, cinnamyl alcohol, 1-cyclohexene-3-ol and oleyl alcohol.

Other specific alcohols useful as reactant (b) are the ether alcohols and amino alcohols including, for example, the oxyalkylene, oxy-arylene-, amino-alkylene-, and amino-arylene-substituted alcohols having one or more oxyalkylene, aminoalkylene or amino-aryleneoxy-arylene radicals. They are exemplified by Cellosolve, carbitol, phenoxyethanol, heptyl phenyl-(oxypropylene)$_6$-OH, octyl-(oxyethylene)$_{30}$-OH, phenyl-(oxyoctylene)$_2$-OH, mono-(heptylphenyl-oxypropylene)-substituted glycerol, poly(styreneoxide), aminoethanol, 3-aminoethylpentanol, di(hydroxyethyl)amine, p-aminophenol, tri(hydroxypropyl)amine, N-hydroxyethyl ethylenediamine, N,N,N',N'-tetrahydroxytrimethylenediamine, and the like.

The polyhydric alcohols preferably contain from 2 to about 10 hydroxy radicals. They are illustrated, for example, by the alkylene glycols and polyoxyalkylene glycols mentioned above such as ethylene glycol, diethylene glycol, triethylene glycol, tetraethylene glycol, dipropylene glycol, tripropylene glycol, dibutylene glycol, tributylene glycol, and other alkylene glycols and polyoxyalkylene glycols in which the alkylene radicals contains 2 to about 8 carbon atoms.

Other useful polyhydric alcohols include glycerol, monooleate of glycerol, monostearate of glycerol, monomethyl ether of glycerol, pentaerythritol, n-butyl ester of 9,10-dihydroxy stearic acid methyl ester of 9,10-dihydroxy stearic acid, 1,2-butanediol, 2,3-hexanediol, 2,4-hexane diol, pinacol, erythritol, arabitol, sorbitol, mannitol, 1,2-cyclohexanediol, and xylene glycol. Carbohydrates such as sugars, starches, celluloses, and so forth likewise can be used as reactant (b). The carbohydrates may be exemplified by glucose, fructose, sucrose, rhamnose, mannose, glyceraldehyde, and galactose.

Polyhydric alcohols having at least 3 hydroxyl groups, some, but not all of which have been esterified with an aliphatic monocarboxylic acid having from about 8 to about 30 carbon atoms such as octanoic acid, oleic acid, stearic acid, linoleic acid. dodecanoic acid or tall oil acid are useful as reactant (b). Further specific examples of such partially esterified polyhydric alcohols are the monooleate of sorbitol, distearate of sorbitol, monooleate of glycerol, monostearate of glycerol, di-dodecanoate of erythritol, and the like.

A preferred class of alcohols suitable as reactant (b) are those polyhydric alcohols containing up to about 12 carbon atoms, and especially those containing 3 to 10 carbon atoms. This class of alcohols includes glycerol, erythritol, pentaerythritol, dipentaerythritol, gluconic acid, glyceraldehyde, glucose, arabinose, 1,7-heptanediol, 2,4-heptanediol, 1,2,3-hexanetriol, 1,2,4-hexanetriol, 1,2,5-hexanetriol, 2,3,4-hexanetriol, 1,2,3-butanetriol, 1,2,4-butanetriol, 2,2,6,6-tetrakis-(hydroxymethyl)cyclohexanol, 1,10-decanediol, digitalose, and the like. Aliphatic alcohols containing at least three hydroxyl groups and up to 10 carbon atoms are particularly preferred.

From what has been stated above, it is seen that amine reactant (a) may contain alcoholic hydroxy substituents and alcohol reactant (b) can contain primary, secondary, or tertiary amino substituents. Thus, amino alcohols can fall into both (a) and (b) provided they contain at least one primary or secondary amino group. If only tertiary amino groups are present, the amino alcohol belongs only in the reactant (b) group.

Amino alcohols contemplated as suitable for use as (a) and/or (b) have one or more amine groups and one or more hydroxy groups. Examples of suitable amino alcohols are the N-(hydroxy-lower alkyl)amines and polyamines such as 2-hydroxyethylamine, 3-hydroxybutylamine, di-(2-hydroxyethyl)-amine, tri-(2-hydroxyethyl)amine, N,N,N'-tri-(2-hydroxyethyl)ethylenediamine, N-(2-hydroxyethyl)piperazine, N-(2-hydroxyethyl)morpholine, N-(2-hydroxyethyl)-2-morpholinone, N-(2-hydroxyethyl)-3-methyl-2-morpholinone, N-(2-hydroxyethyl)-5-carbethoxy-2-piperidone, N-(2-hydroxypropyl)-5-carbethoxy-2-piperidone, N-(4-hydroxybutyl)piperidine, N,N-di-(2-hydroxyethyl)glycine, and ethers thereof with aliphatic alcohols, especially lower alkanols, N,N-di-(3-hydroxypropyl)glycine, and the like. Also contemplated are other mono- and poly-N-hydroxyalkyl-substituted alkylene polyamines wherein the alkylene polyamine are as described above; especially those that contain 2 to 3 carbon atoms in the alkylene radicals and the alkylene polyamine contains up to 7 amino groups such as the reaction product of about two moles of propylene oxide and one mole of diethylenetriamine.

Further amino alcohols are the hydroxy-substituted primary amines described in U.S. Pat. No. 3,576,743 by the general formula $$R_a\text{—}NH_2 \qquad \text{(XII)}$$

wherein $R_a$ is a monovalent organic radical containing at least one alcoholic hydroxyl group and up to about 20 carbon atoms. Hydroxy-substituted aliphatic primary amines containing a total of up to about 10 carbon atoms are particularly useful. Especially preferred are the polyhydroxy-substituted alkanol primary amines wherein there is only one amino group present (i.e., a primary amino group) having one alkyl substituent containing up to 10 carbon atoms and up to 6 hydroxyl groups. These alkanol primary amines correspond to $R_a\text{—}NH_2$ wherein $R_a$ is a mono- or polyhydroxy-substituted alkyl group. It is desirable that at least one of the hydroxyl groups be a primary alcoholic hydroxyl group. Trismethylolaminomethane is the single most preferred hydroxy-substituted primary amine. Specific examples of the hydroxy-substituted primary amines include 2-amino-1-butanol, 2-amino-2-methyl-1-propanol, p-(beta-hydroxyethyl)-aniline, 2-amino-1-propanol, 3-amino-1-propanol, 2-amino-2-methyl-1,3-propanediol, N-(beta-hydroxypropyl)-N'-beta-aminoethyl)-piperazine, tris(hydroxymethyl)amino methane (also known as trismethylolamino methane). 2-amino-1-butanol, ethanolamine, beta-(beta-hydroxy ethoxy)e-thylamine, 4-amino-3-hydroxy-3-methyl-1-butene (which can be prepared according to procedures known in the art by reacting isopreneoxide with ammonia), N-(3-aminopropyl)-4-(2-hydroxyethyl)-piperadine, 2-amino-6-methyl-6-hepanol, 5-amino-1-pentanol, 1,3-diamino- 2-hydroxy-propane, N-(beta-hydroxy ethoxyethyl)-ethylenediamine, and the like. For further description of the hydroxy-substituted primary amines contemplated as being useful as reactants (a). and/or (b), U.S. Pat. No. 3,576,743 is expressly incorporated herein by reference for its disclosure of such amines.

The carboxylic derivative compositions produced by reacting the acylating reagents of this invention with alcohols are esters. Both acidic esters and neutral esters are contemplated as being within the scope of this invention. Acidic esters are those in which some of the carboxylic acid functions in the acylating reagents are not esterified but are present as free carboxyl groups. Obviously, acid esters are easily prepared by using an amount of alcohol insufficient to esterify all of the carboxyl groups in the acylating reagents of this invention.

The acylating reagents of this invention are reacted with the alcohols according to conventional esterification techniques. This normally involves heating the acylating reagent of this invention with the alcohol, optionally in the presence of a normally liquid, substantially inert, organic liquid solvent/diluent and/or in the presence of esterification catalyst. Temperatures of at least about 100° C. up to the decomposition point are used (the decomposition point having been defined hereinbefore). This temperature is usually within the range of about 100° C. up to about 300° C. with temperatures of abut 140° C. to 250° C. often being employed. Usually, at least about one-half equivalent of alcohol is used for each equivalent of acylating reagent. An equivalent of acylating reagent is the same as discussed above with respect to reaction with amines. An equivalent of alcohol is its molecular weight divided by the total number of hydroxyl groups present in the molecule. Thus, an equivalent weight of ethanol is its molecular weight while the equivalent weight of ethylene glycol is one-half its molecular weight.

Many issued patents disclose procedures for reacting high molecular weight carboxylic acid acylating agents with alcohols to produce acidic esters and neutral esters. These same techniques are applicable to preparing esters from the acylating reagents of this invention and the alcohols described above. All that is required is that the acylating reagents of this invention is substituted for the high molecular weight carboxylic acid acylating agents discussed in these patents, usually on an equivalent weight basis. The following U.S. patents are expressly incorporated herein by reference for their disclosure of suitable methods for reacting the acylating reagents of this invention with the alcohols described above: 3,331,776; 3,381,022; 3,522,179; 3,542,680; 3,697,428; and 3,755,169.

Reactive metals or reactive metal compounds useful as reactant (c) are those which will form carboxylic acid metal salts with the acylating reagents of this invention and those which will form metal-containing complexes with the carboxylic derivative compositions produced by reacting the acylating reagents with amines and/or alcohols as discussed above. Reactive metal compounds useful as reactant (c) for the formation of complexes with the reaction products of the acylating reagents of this invention and amines are disclosed in U.S. Pat. No. 3,306,908. Complex-forming metal reactants useful as reactant (c) include the nitrates, nitrites, halides, carboxylates, phosphates, phosphites, sulfates, sulfites, carbonates, borates, and oxides of cadmium as well as metals having atomic numbers from 24 to 30 (including chromium, manganese, iron, cobalt, nickel, copper and zinc). These metals are the so-called transition or co-ordination metals, i.e., they are capable of forming complexes by means of their secondary or co-ordination valence. Specific examples of the complex-forming metal compounds useful as the reactant in this invention are cobaltous nitrate, cobaltous oxide, cobaltic oxide, cobalt nitrite, cobaltic phosphate, cobaltous chloride, cobaltic chloride, cobaltous carbonate, chromous acetate, chromic acetate, chromic bromide, chromous chloride, chromic fluoride, chromous oxide, chromium dioxide, chromic oxide, chromic sulfite, chromous sulfate heptahydrate, chromic sulfate, chromic formate, chromic hexanoate, chromium oxychloride, chromic phosphite, manganous acetate, manganous benzoate, manganous carbonate, manganese dichloride, manganese trichloride, manganous citrate, manganous formate, manganous nitrate, manganous oxalate, manganese monoxide, manganese dioxide, manganese trioxide, manganese heptoxide, manganic phosphate, manganous pyrophosphate, manganic metaphosphate, manganous hypophosphite, manganous valerate, ferrous acetate, ferric benzoate, ferrous bromide, ferrous carbonate, ferric formate, ferrous lactate, ferrous nitrate, ferrous oxide, ferric oxide, ferric hypophosphite, ferric sulfate, ferrous sulfite, ferric hydrosulfite, nickel dibromide, nickel dichloride, nickel nitrate, nickel dioleate, nickel stearate, nickel sulfite, cupric propionate, cupric acetate, cupric metaborate, cupric benzoate, cupric formate, cupric laurate, cupric nitrate, cupric oxychloride, cupric palmitate, cupric salicylate, zinc benzoate zinc borate, zinc bromide, zinc chromate, zinc dichromate, zinc iodide, zinc lactate zinc nitrate, zinc oxide, zinc stearate, zinc sulfite, cadmium benzoate, cadmium carbonate, cadmium butyrate, cadmium chloroacetate, cadmium fumerate, cadmium nitrate, cadmium di-hydrogenphosphate, cadmium sulfite, and cadmium oxide. Hydrates of the above compounds are especially convenient for use in the process of this invention.

U.S. Pat. No. 3,306,908 is expressly incorporated herein by reference for its discussion of reactive metal compounds suitable for forming such complexes and its disclosure of processes for preparing the complexes. Basically, those processes are applicable to the carboxylic derivative compositions of the acylating reagents of this invention with the amines as described above by substituting, or on an equivalent basis, the acylating reagents of this invention with the high molecular weight carboxylic acid acylating agents disclosed in the '908 patent. The ratio of equivalents of the acylated amine thus produced and the complex-forming metal reactant remains the same as disclosed in the '908 patent.

U.S. Pat. No. 26,443 discloses metals useful in preparing salts from the carboxylic derivative compositions of acylating reagents of this invention and amines as described hereinabove. Metal salts are prepared, according to this patent, from alkali metals, alkaline earth metals, zinc, cadmium, lead, cobalt and nickel. Examples of a reactive metal compound suitable for use as reactant (c) are sodium oxide, sodium hydroxide, sodium carbonate, sodium methylate, sodium propylate, sodium pentylate, sodium phenoxide, potassium oxide, potassium hydroxide, potassium carbonate, potassium methylate, potassium pentylate, potassium phenoxide, lithium oxide, lithium hydroxide, lithium carbonate, lithium pentylate, calcium oxide, calcium hydroxide, calcium carbonate, calcium methylate, calcium ethylate, calcium propylate, calcium chloride, calcium fluoride, calcium pentylate, calcium phenoxide, calcium nitrate, barium oxide, barium hydroxide, barium carbonate, barium chloride, barium fluoride, barium methylate, barium propylate, barium pentylate, barium nitrate, magnesium oxide, magnesium hydroxide, magnesium carbonate, magnesium ethylate, magnesium propylate, magnesium chloride, magnesium bromide, barium, iodide, magnesium phenoxide, zinc oxide, zinc hydroxide, zinc carbonate, zinc methylate, zinc propylate, zinc pentylate, zinc chloride, zinc fluoride, zinc nitrate trihydrate, cadmium oxide, cadmium hydroxide, cadmium carbonate cadmium methylate, cadmium propylate, cadmium chloride, cadmium bromide, cadmium fluoride, lead oxide, lead hydroxide, lead carbonate, lead ethylate, lead pentylate, lead chloride, lead fluoride, lead iodide, lead nitrate, nickel oxide, nickel hydroxide, nickel carbonate, nickel chloride, nickel bromide, nickel fluoride, nickel methylate, nickel pentylate, nickel nitrate hexahydrate, cobalt oxide, cobalt hydroxide, cobaltous bromide, cobaltous chloride, cobalt butylate, cobaltous nitrate hexahydrate, etc. The above metal compounds are merely illustrative of those useful in this invention and the invention is not to be considered as limited to such.

U.S. Pat. No. 26,443 is expressly incorporated herein by reference for its disclosure of reactive metal compounds useful as reactant (c) and processes for utilizing these compounds in the formation of salts. Again, in applying the teachings of this patent to the present invention, it is only necessary to substitute the acylating reagents of this invention on an equivalent weight basis for the high molecular weight carboxylic acylating agents of the reissue patent.

U.S. Pat. No. 3,271,310 discloses the preparation of metal salts of high molecular weight carboxylic acid acylating agents, in particular alkenyl succinic acids. The metal salts disclosed therein are acid salts, neutral salts, and basic salts. Among the illustrative reactive metal compounds used to prepare the acidic, neutral and basic salts of the high molecular weight carboxylic acids disclosed in the '310 patent are lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate barium pentylate, aluminum oxide, aluminum propylate lead oxide, lead hydroxide, lead carbonate, tin oxide, tin butylate, cobalt oxide, cobalt hydroxide, cobalt carbonate, cobalt pentylate, nickel oxide, nickel hydroxide, and nickel carbonate. The present invention is not to be considered as limited to the use of the above metal compounds; they are presented merely to illustrate the metal compounds included within the invention.

U.S. Pat. No. 3,271,310 is expressly incorporated herein by reference for its disclosure of suitable reactive metal compounds for forming salts of the acylating reagents of this invention as well as illustrative processes for preparing salts of these acylating reagents. As will be apparent, the processes of the '310 patent are applicable to the acylating reagents of this invention merely by substituting on an equivalent weight basis, the acylating reagents of this invention for the high molecular weight carboxylic acids of the patent.

From the foregoing description, it is apparent that the acylating reagents of this invention can be reacted with any individual amine, alcohol, reactive metal, reactive metal compound or any combination of two or more of any of these. Furthermore, the acylating reagents of this invention can be reacted with the amines, alcohols, reactive metals, reactive metal compounds, or mixtures thereof, as described above, simultaneously (concurrently) or sequentially in any order of reaction.

Canadian patent 956,397 is expressly incorporated herein by reference for its disclosure of procedures for reacting the acylating reagents of this invention with amines, alcohols, reactive metal and reactive metal compounds, or mixtures of these, sequentially and simultaneously. All that is required to apply the processes of that patent to this invention is to substitute, on an equivalent weight basis, the acylating reagents of this invention for the high molecular weight carboxylic acid acylating agents disclosed in that Canadian patent. Substituted carboxylic acid derivatives of this invention prepared utilizing the processes disclosed in the Canadian patent constitute a preferred class of carboxylic acids or carboxylic acid derivative compositions. The following U.S. patents are also incorporated herein by reference: U.S. Pat. Nos. 3,836,469; 3,836,470;

3,836,471; 3,838,050; 3,838,052; 3,879,308; 3,957,854; 3,957,855.

In addition, U.S. Pat. No. 3,806,456 is expressly incorporated herein by reference for its disclosure of processes useful in preparing products from the acylated reagents of this invention and polyoxyalkylene polyamines as described hereinbefore. Substitution of the acylated reactants of this invention for the high molecular weight carboxylic acid acylating agents disclosed in the '456 patent on an equivalent weight basis produces compounds of similar utility further characterized by the desired viscosity index improving properties discussed hereinbefore.

U.S. Pat. No. 3,576,743 is also incorporated herein by reference for its disclosure of a process for preparing carboxylic derivative compositions from both polyhydric alcohols and amine; in particular, hydroxy-substituted primary amines. Again, substitution of the acylating reagents of this invention on an equivalent weight basis for the high molecular carboxylic acid acylating agents disclosed in the '743 patent provides compositions having the desired dispersant/detergent compositions and the V.I. improving properties already discussed.

U.S. Pat. No. 3,632,510 is expressly incorporated herein by reference for its disclosure of processes for preparing mixed ester-metal salts. Mixed ester-metal salts derived from acylating reagents of this invention, the alcohols, and the reactive metal compounds can be prepared by following the processes disclosed in the '510 patent but substituting, on an equivalent weight basis, the acylating reagents of this invention for the high molecular weight carboxylic acid acylating agents of the patent. The carboxylic acid derivative compositions thus produced also represent a preferred aspect of this invention.

Finally, U.S. Pat. Nos. 3,755,169; 3,804,763; 3,868,330; and 3,948,800 are expressly incorporated herein by reference for their disclosure of how to prepare carboxylic acid derivative compositions. By following the teachings of these patents and substituting the acylating reagents of this invention for the high molecular weight carboxylic acylating agents of the patents, a wide range of carboxylic derivative compositions within the scope of the present invention can be prepared.

Incorporation of so many patents is done for the sake of brevity and because the procedures necessary to prepare the carboxylic derivative compositions from the acylating reagents and the amines, alcohols, and reactive metals and reactive metal compounds, as well as mixtures thereof, are well within the skill of the art, such that a detailed description herein is not necessary.

Of the carboxylic derivative compositions described hereinabove, those prepared from novel acylating reagents and the alkylene polyamines, especially polyethylene polyamines, and/or polyhydric alcohols, especially the polyhydric alkanols, are especially preferred. As previously stated, mixtures of polyamines and/or polyhydric alcohols are contemplated. Normally, all the carboxyl functions on the acylating reagents of this invention will either be esterified or involved in formation of an amine salt, amide, imide or imidazoline in this preferred group of carboxylic derivative compositions.

Another aspect of this invention involves the post-treatment of the substituted carboxylic acid derivative compositions. The process for post-treating the carboxylic acid derivative compositions is again analogous to the post-treating processes used with respect to similar derivatives of the high molecular weight carboxylic acid acylating agents of the prior art. Accordingly, the same reaction conditions, ratio of reactants and the like can be used.

Acylated nitrogen compositions prepared by reacting there acylating reagents of this invention with an amine as described above are post-treated by contacting the acylated nitrogen compositions thus formed (e.g., the carboxylic derivative compositions) with one or more post-treating reagents selected from the group consisting of boron oxide, boron oxide hydrate, boron halides, boron acids, esters of boron acids, carbon disulfide, sulfur, sulfur chlorides, alkenyl cyanides, carboxylic acid acylating agents, aldehydes, ketones, urea, thiourea, guanidine, dicyanodiamide, hydrocarbyl phosphates, hydrocarbyl phosphites, hydrocarbyl thiophosphates, hydrocarbyl thiophosphites, phosphorus sulfides, phosphorus oxides, phosphoric acid, hydrocarbyl thiocyanates, hydrocarbyl isocyanates, hydrocarbyl isothiocyanates, epoxides, episulfides, formaldehyde or formaldehyde-producing compounds with phenols, and sulfur with phenols. The same post-treating reagents are used with carboxylic derivative compositions prepared from the acylating reagents of this invention and a combination of amines and alcohols as described above. However, when the carboxylic derivative compositions of this invention are derived from alcohols and the acylating reagents, that is, when they are acidic or neutral esters, the post-treating reagents are usually selected from the group consisting of boron oxide, boron oxide hydrate, boron halides, boron acids, esters of boron acids, sulfur, sulfur chlorides, phosphorus sulfides, phosphorus oxides, carboxylic acid acylating agents, epoxides, and episulfides.

Since post-treating processes involving the use of these post-treating reagents is known insofar as application to reaction products of high molecular weight carboxylic acid acylating agents of the prior art and amines and/or alcohols, detailed description of these processes herein is unnecessary. In order to apply the prior art processes to the carboxylic derivative compositions of this invention, all that is necessary is that reaction conditions, ratio of reactants, and the like as described in the prior art, be applied to the novel carboxylic derivative compositions of this invention. The following U.S. patents are expressly incorporated herein by reference for their disclosure of post-treating processes and post-treating reagents applicable to the carboxylic derivative compositions of this invention: U.S. Pat. Nos. 3,087,936; 3,200,107; 3,254,025; 3,256,185; 3,278,550; 3,281,428; 3,282,955; 3,284,410; 3,338,832; 3,344,069; 3,366,569; 3,373,111; 3,367,943; 3,403,102; 3,428,561; 3,502,677; 3,513,093; 3,533,945; 3,541,012 (use of acidified clays in post-treating carboxylic derivative compositions derived from the acylating reagents of this invention and amines): 3,639,242; 3,708,522; 3,859,318; 3,865,813; 3,470,098; 3,369,021; 3,184,411; 3,185,645; 3,245,908; 3,245,909; 3,245,910; 3,573,205; 3,269,681; 3,749,695; 3,865,740; 3,954,639; 3,459,530; 3,390,086; 3,367,943; 3,185,704; 3,551,466; 3,415,750; 3,312,619; 3,280,034; 3,718,663; 3,652,616; 3,558,743; U.K. patents: 1,085,903; 1,162,436. The processes of these incorporated patents, as applied to the carboxylic derivative compositions of this invention, and the post-treated carboxylic derivative compositions thus produced constitute a further aspect of this invention.

As previously indicated, the acylating reagents, the carboxylic derivative compositions, and the post-treated carboxylic derivative compositions of this invention are useful as additives in lubricating oils. The acylating reagents, the carboxylic derivative compositions, and the post-treated carboxylic derivative compositions, especially the latter two, function primarily as dispersant/detergents and viscosity index improvers.

EXAMPLE 1

A mixture of 281 parts (7 equivalents) of tetraethylene pentamine and 2027 parts of mineral oil is prepared and heated to a temperature of 150° C. whereupon 2805 parts (5 equivalents) of the substituted succinic acylating agent prepared in Example A are added over a period of one hour. The temperature is raised to about 160° C. and maintained at this temperature for four hours while removing water from the reaction mixture. The reaction mixture is filtered to yield a filtrate as an oil solution of the desired derivative. A yield of 94% of theory is obtained, and the product contains about 2% nitrogen.

EXAMPLE 2

A mixture is prepared by the addition of 10.2 parts (0.25 equivalent) of a commercial mixture of ethylene polyamines having from about 3 to about 10 nitrogen atoms per molecule to 113 parts of mineral oil and 140 parts (0.25 equivalent) of the substituted succinic acylating agent prepared in Example A at 138° C. The reaction mixture is heated to 150° C. in two hours and stripped by blowing with nitrogen. The reaction mixture is filtered to yield the filtrate as an oil solution of the desired product.

EXAMPLE 3

A mixture of 292 parts (0.52 equivalent) of the polyisobutene substituted succinic acylating agent prepared in Example A, 548 parts of mineral oil, 30 parts (0.88 equivalent) of pentaerythritol and 8.6 parts (0.0057 equivalent) of polyglycol 112-2 demulsifier from Dow Chemical Company is heated at 150° C. for 2.5 hours. The reaction mixture is heated to 210° C. in five hours and held at 210° C. for 3.2 hours. The reaction mixture is cooled to 190° C. and 8.5 parts (0.2 equivalent) of a commercial mixture of ethylene polyamines having an average of about 3 to about 10 nitrogen atoms per molecule is added. The reaction mixture is stripped by heating at 205° C. with nitrogen blowing for three hours, then filtered to yield the
filtrate as an oil solution of the desired product.

EXAMPLES 4–22

Examples 4–22 are prepared by following the general procedure set forth in Example 2.

TABLE I

| Example Number | Succinic Acylating Agent Prepared | Reactant(s) | Ratio of Substituted Succinic Acylating Agent to Reactants | % Diluent |
|---|---|---|---|---|
| 4 | Example A | Pentaethylene hexamine[a] | 1:2 equivalents | 40% |
| 5 | Example A | ZnO[b]:polyamines[c] | 1:0.5:0.5 equivalents | 50% |
| 6 | Example B | Tris(2-aminoethyl)amine | 2:1 moles | 50% |
| 7 | Example B | Imino-bis-propylamine | 2:1 moles | 40% |
| 8 | Example B | Hexamethylene diamine | 1:2 moles | 40% |
| 9 | Example E | 1-(2-Aminoethyl)-2-methyl-2-imidazoline | 1:1 equivalents | 40% |
| 10 | Example C | N-aminopropylpyrrolidone | 1:1 moles | 40% |
| 11 | Example D | N,N-dimethyl-1,3-Propane diamine | 1:1 equivalents | 40% |
| 12 | Example E | N-(2-hydroxyethyl)-ethylene diamine | 1:1 equivalents | 40% |
| 13 | Example E | 1-amino-2-propanol | 1:1 equivalents | 40% |
| 14 | Example A | Ethylene diamine | 1:4 equivalents | 40% |
| 15 | Example A | 1,3-Propane diamine | 1:1 moles | 40% |
| 16 | Example B | 2-Pyrrolidinone | 1:1.1 mole | 20% |
| 17 | Example C | Urea | 1:0.6 mole | 50% |
| 18 | Example A | Diethylenetriamine[d] | 1:1 mole | 50% |
| 19 | Example A | Triethylenetetramine[e] | 1:0.5 mole | 50% |
| 20 | Example E | Aminoglycerol | 1:1 mole | 50% |
| 21 | Example E | Ethanolamine | 1:1 mole | 45% |
| 22 | Example E | Tris(hydroxymethyl)aminomethane:polyamines[c] | 10:1:7 equivalents | 55% |

[a] A commercial mixture of ethylene polyamines corresponding in empirical formula to pentaethylene hexamine.
[b] In this example the ZnO is added with water to the polyisobutene-substituted succinic acylating agent and mineral oil mixture at 78° C., heated at 95° C. for four hours and then the preparation is completed according to the general procedure set forth in Example 10.
[c] A commercial mixture of ethylene polyamines having an average of 3–10 nitrogen atoms per molecule.
[d] A commercial mixture of ethylene polyamines corresponding in empirical formula to diethylenetriamine.
[e] A commercial mixture of ethylene polyamines corresponding in empirical formula to triethylenetetramine.

EXAMPLE 23

A mixture of 2130 parts (1.5 moles) of the polyisobutene-substituted succinic acylating agent prepared in Example A, 187 parts (1.65 moles) of caprolactam, 575 parts of mineral oil and 2 parts of sodium hydroxide is heated at 190°–193° C. for two hours. The reaction mixture is stripped at 200° C. under vacuum and filtered at 150° C. to yield an oil solution of the desired product.

EXAMPLE 24

A mixture of 3225 parts (5.0 equivalents) of the polyisobutene-substituted succinic acylating agent prepared in Example A, 289 parts (8.5 equivalents) of pentaerythritol and 5204 parts of mineral oil is heated at 225°–235° C. for 5.5 hours. The reaction mixture is filtered at 130° C. to yield an oil solution of the desired product.

EXAMPLE 25

A mixture of 631 parts of the oil solution of the product prepared in Example 24 and 50 parts of anthranilic acid is heated at 195°–212° C. for four hours. The reaction mixture is then filtered at 130° C. to yield an oil solution of the desired product.

EXAMPLE 26

A mixture is prepared by the addition of 14 parts of aminopropyl diethanolamine to 867 parts of the oil solution of the product prepared in Example 24 at 190°–200° C. The reaction mixture is held at 195° C. for 2.25 hours, then cooled to 120° C. and filtered. The filtrate is an oil solution of the desired product.

EXAMPLE 27

A mixture is prepared by the addition of 7.5 parts of piperazine to 867 parts of the oil solution of the product prepared in Example 24 at 190° C. The reaction mixture is heated at 190°–205° C. for two hours, then cooled to 130° C. and filtered. The filtrate is an oil solution of the desired product.

EXAMPLE 28

A mixture of 322 parts (0.5 equivalent) of the polyisobutene-substituted succinic acylating agent prepared in Example B, 68 parts (2.0 equivalents) of pentaerythritol and 508 parts of miner oil is heated at 204°–227° C. for five hours. The reaction mixture is cooled to 162° C. and 5.3 parts (0.13 equivalent) of a commercial ethylene polyamine mixture having an average of about 3 to 10 nitrogen atoms per molecule is added. The reaction mixture is heated at 162°–163° C. for one hour, then cooled to 130° C. and filtered. The filtrate is an oil solution of the desired product.

EXAMPLE 29

A mixture of 1480 parts of the polyisobutene-substituted succinic acylating agent prepared in Example A, 115 parts (0.53 equivalent) of a commercial mixture of $C_{12-18}$ straight-chain primary alcohols, 87 parts (0.594 equivalent) of a commercial mixture of $C_{8-10}$ straight-chain primary alcohols, 1098 parts of mineral oil and 400 parts of toluene is heated to 120° C. At 120° C., 1.5 parts of sulfuric acid is added and the reaction mixture is heated to 160° C. and held for three hours. To the reaction mixture is then added 158 parts (2.0 equivalents) of n-butanol and 1.5 parts of sulfuric acid. The reaction mixture is heated at 160° C. for 15 hours, then 12.6 parts (0.088 equivalent) of aminopropyl morpholine is added. The reaction mixture is held at 160° C. for an additional six hours, stripped at 150° C. under vacuum and filtered to yield an oil solution of the desired product.

EXAMPLE 30

A mixture of 328 parts (0.5 equivalent) of the polyisobutene-substituted succinic acylating agent prepared in Example A, 129 parts (1.0 equivalent) of 1-(2-hydroxyethyl)-2-pyrrolidone and 359 parts of mineral oil is heated at 190° C. for four hours. During the four hours at 190° C., water is removed continuously by blowing with nitrogen. The reactive mixture is filtered to yield the filtrate as an oil solution of the desired product.

EXAMPLE 31

A mixture is prepared by the addition of 31 parts of carbon disulfide over a period of 1.66 hours to 853 parts of the oil solution of the product prepared in Example 4 at 113°–145° C. The reaction mixture is held at 145°–152° C. for 3.5 hours, then filtered to yield an oil solution of the desired product.

EXAMPLE 32

A mixture of 62 parts of boric acid and 2720 parts of the oil solution of the product prepared in Example 2 is heated at 150° C. under nitrogen for six hours. The reaction mixture is filtered to yield the filtrate as an oil solution of the desired boron-containing product.

EXAMPLE 33

An oleyl ester of boric acid is prepared by heating an equimolar mixture of oleyl alcohol and boric acid in toluene at the reflux temperature while water is removed azeotropically. The reaction mixture is then heated to 150° C. under vacuum and the residue is the ester having a boron content of 3.2% and a saponification number of 62. A mixture of 344 parts of the ester and 2720 parts of the oil solution of the product prepared in Example 2 is heated at 150° C. for six hours and then filtered. The filtrate is an oil solution of the desired boron-containing product.

EXAMPLE 34

A mixture of 3420 parts of the oil-containing solution of the product prepared in Example 4 and 53 parts of acrylonitrile is heated at reflux temperature from 125° C. to 145° C. for 1.25 hours, at 145° C. for three hours and then stripped at 125° C. under vacuum. The residue is an oil solution of the desired product.

EXAMPLE 35

A mixture is prepared by the addition of 44 parts of ethylene oxide over a period of one hour to 1460 parts of the oil solution of the product prepared in Example 4 at 150° C. The reaction mixture is held at 150° C. for one hour, then filtered to yield the filtrate as an oil solution of the desired product.

EXAMPLE 36

A decyl ester of phosphoric acid is prepared by adding one mole of phosphorus pentoxide to three moles of decyl alcohol at a temperature within the range of 32° C. to 55° C. and then heating the mixture at 60°–63° C. until the reaction is complete. The product is a mixture of decyl esters of phosphoric acid having a phosphorus content of 9.9% and an acid number of 250 (phenolphthalein indicator). A mixture of 1750 parts of the oil solution of the product prepared in Example 2 and 112 parts of the above decyl ester is heated at 145°–150° C. for one hour. The reaction mixture is filtered to yield the filtrate as an oil solution of the desired product.

EXAMPLE 37

A mixture of 2920 parts of the oil solution of the product prepared in Example 1 and 69 parts of thiourea is heated to 80° C. and held at 80° C. for two hours. The reaction mixture is then heated to 150°–155° C. for four hours, the last of which the mixture is blown with nitrogen. The reaction mixture is filtered to yield the filtrate as an oil solution of the desired product.

EXAMPLE 38

A mixture of 1160 parts of the oil solution of the product prepared in Example 4 and 67 parts of sulfur monochloride is heated for one hour at 150° C. under nitrogen. The mixture is filtered to yield an oil solution of the desired sulfur-containing product.

EXAMPLE 39

A mixture is prepared by the addition of 58 parts of propylene oxide to 1170 parts of the oil solution of the product prepared in Example 24 and 10 parts of pyridine at 80°–90° C. The reaction mixture is then heated at 100°–120° C. for 2.5 hours and then stripped to 170° C. under vacuum. The residue is an oil solution of the desired product.

EXAMPLE 40

A mixture of 1000 parts of the oil solution of the product prepared in Example 28 and 10 parts of sulfur is heated at 160° C. for two hours, then at 160°–180° C. for one hour. The reaction mixture is cooled to 120° C. and filtered to yield the filtrate as an oil solution of the desired product.

EXAMPLE 41

A reactor equipped with a column, condenser receiver and stirrer is charged with 255 parts mineral diluent oil and 38.4 parts tetraethylene pentamine. A slight nitrogen purge is placed on the reactor via a non-submerged line and 350 parts of the product of Example E are added to the reactor over eight hours. During the addition, heating is used to increase the batch temperature to 120° in 4.5 hours and then the temperature is maintained at 120° for the remainder of the addition. Following the addition period, the temperature is increased to 150° over 3.5 hours. The nitrogen purge is redirected to a submerged line. The reaction mixture is nitrogen blown for one hour at 150°–155°, then filtered at 140°–145° using a diatomaceous earth filter aid. The filtrate is the desired product.

EXAMPLE 42

To a 12-liter reactor equipped with a stirrer thermowell, nitrogen inlet, Dean Stark trap and condenser, there is charged 281 parts tetraethylene pentamine and 2028 parts mineral oil diluent. The solution is heated to 115° and 2805 parts of the reaction product of Example C. is added over 1.5 hours. The reaction mixture is heated to 160° and held at that temperature for four hours. The material is cooled to 120° and filtered with a diatomaceous earth filter aid. The filtrate is the product.

EXAMPLE 43

A one-liter reactor equipped as described in Example 42 is charged with 24.1 parts tetraethylene pentamine and 160.3 parts mineral oil diluent. The materials are heated to 115° followed by addition of 220 parts of the reaction product of Example D over 15 minutes. The temperature is raised to 160° and held for four hours. The materials are cooled to 120° and filtered with a diatomaceous earth filter aid. The clear filtrate is the product.

EXAMPLE 44

To a 12-liter reactor equipped as described in Example 43, there is charged 2057 parts mineral oil diluent and 272 parts tetraethylene pentamine. The solution is heated to 115° and 2860 parts of the reaction product of Example D are added over one hour. The reaction mixture is heated to 160° and held for four hours. The reaction product is filtered at 120° with a diatomaceous earth filter aid. The filtrate is the desired product.

EXAMPLE 45

A five-liter reactor equipped as described in Example 42 is charged with 215.8 parts tetraethylene pentamine and 1283 parts mineral diluent oil. The solution is heated to 110°, and over a period of 45 minutes, there is added 1734 parts of the product of Example E. The reaction mixture is heated to 150° and held for four hours. The reaction product is filtered at 120°. The clear filtrate is the desired product.

EXAMPLE 46

A five-liter reactor equipped as described in Example 42 is charged with 1850 parts of the reaction product of Example E and 1280 parts of mineral diluent oil. The solution is heated to 110° followed by addition of 99.1 parts of tetraethylene pentamine over 0.5 hours while the temperature increases exothermically to 120°. The reaction mixture is heated to 150° and held for four hours. The material is filtered at 120° with a diatomaceous earth filter aid. The clear filtrate is the desired product.

EXAMPLE 47

A 12-liter reactor equipped as described in Example 42 is charged with 3296 parts mineral diluent oil, 91 parts triethylene tetramine and 302 parts tetraethylene pentamine. The solution is heated to 115°, and 4658 parts of the reaction product of Example E is added over 1.75 hours. The mixture is heated to 160° and held at 160° for four hours. The reaction mixture is filtered at 130° using a diatomaceous earth filter aid. The clear filtrate is the desired product

EXAMPLE 48

A one-liter reactor equipped as described in Example 42 is charged with 40.15 parts triethylene tetramine and 406 parts mineral diluent oil. The solution is heated to 115, and 578 parts of the reaction product of Example E is added over 0.5 hour. The mixture is heated to 160° and held at 160° for four hours. The reaction product is cooled to 120° and filtered with a diatomaceous earth filter aid. The filtrate is the desired product.

EXAMPLE 49

The procedure of Example 48 is repeated except 301.5 parts tetraethylene pentamine. 2477 parts mineral diluent oil and 3468 parts of the product of Example E are employed.

EXAMPLE 50

A 12-liter reactor equipped as described in Example 42 is charged with 402 parts of tetraethylene pentamine and 3303 parts mineral diluent oil. The solution is heated to 110°, followed by addition of 4624 parts of the reaction product of Example E over two hours. The mixture is heated to 150° and held at 150° for four hours. The materials are filtered at 140° with a diatomaceous earth filter aid. The filtrate is the desired product.

EXAMPLE 51

A one-liter reactor as described in Example 42 is charged with 18.6 parts tetraethylene pentamine and 240 parts mineral diluent oil. The solution is heated to 110° followed by addition of 347 parts of the reaction product of Example E over 0.5 hour. The mixture is heated to 150° and held at 150° for four hours. The reaction product is filtered at 120° using a diatomaceous earth filter aid. The clear filtrate is the desired product.

EXAMPLE 52

The procedure of Example 51 is followed using 41 parts tetraethylene pentamine, 237 parts mineral diluent oil and 320 parts of the reaction product of Example E.

EXAMPLE 53

A two-liter reactor equipped as described in Example 42 is charged with 495 parts mineral diluent oil and 272 parts of the product of Example E. The solution is heated to 110° and 14.6 parts tetraethylene pentamine is added over 5 minutes. The temperature is increased to 150° and the mixture is held at 150° for one hour. The mixture is then cooled to 110° and 57.9 parts tetraethylene pentamine is added over 0.5 hour followed by addition of 413 parts of the reaction product of Example E being added at 110° over 0.5 hour. The reaction mixture is heated to 150° and held at 150° for four hours. The materials are cooled to 120° and filtered using a diatomaceous earth filter aid. The filtrate is the desired product.

EXAMPLE 54

A five-liter reactor equipped as described in Example IV is charged with 1,618 parts of the reaction product of Example E. The material is heated to 150° and 171 parts pentaerythritol is added. The temperature is increased to 203° over 0.75 hours and held at 203° for 16.5 hours. The total acid number is 9.5. The reaction mixture is cooled to 190°, and 29.1 parts of a polyamine mixture having a nitrogen analysis equivalent to tetraethylene pentamine is added over 0.5 hours. The reaction mixture is heated to 210° and held at 210° for one hour. Mineral diluent oil (1467 parts) is added and the material is cooled to 135° and filtered using a diatomaceous earth filter aid. The clear filtrate is the product.

EXAMPLE 55

A one-liter reactor equipped as described in Example 42 is charged with 611 parts of the reaction product of Example 45 and heated to 115° with stirring. A similarly equipped 500 milliliter flask is charged with 25.3 parts boric acid and 55 parts mineral diluent oil. The mixture in the smaller flask is heated at 115° for two hours and then added to the contents of the larger flask. Mineral diluent oil (15 parts) is used to wash out the smaller flask and is then added to the larger flask. The materials are heated for one hour at 115° followed by six hours of heating at 160°. The reaction mixture is filtered using a diatomaceous earth filter aid. The boron- and nitrogen-containing filtrate is the desired product.

EXAMPLE 56

A one-liter reactor as described in Example 55 is charged with 611 parts of the reaction product of Example 45. The material is heated to 80°, and 65.9 parts tap water are added. The temperature is increased to 90°. and 22.6 parts boric acid is added. The mixture is heated to 105°, refluxed for four hours and thereafter dried by removing water which is collected in a Dean Stark trap. The mixture is then stripped to 120° at 0.5 millimeters mercury to remove remaining water. The residue is filtered using a diatomaceous earth filter aid. The filtrate is the desired product.

The above compositions of the invention can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines two-cycle engines, aviation piston engines, marine and railroad diesel engines, and the like. They can also be used in gas engines, stationary power engines and turbines and the like. Automatic transmission fluids transaxle lubricants, gear lubricants, metal-working lubricants, hydraulic fluids and other lubricating oil and grease compositions can also benefit from the incorporation therein of the compositions of the invention.

Natural oils include animal oils and vegetable oils (e.g., castor, lard oil) liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins [e.g., polybutylenes polypropylenes propylene-isobutylene copolymers. chlorinated polybutylenes, poly(1-hexenes), poly(1-octenes), poly(1-decenes)]; alkylbenzenes (e.g. dodecylbenzenes tetradecylbenzenes, dinonylbenzenes. di(2-ethylhexyl)benzenes]; polyphenyls (e.g.. biphenyls, terphenyls, alkylated polyphenols); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherification etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methylpolyisopropylene qlycol ether having an average molecular weight of 1000, diphenyl ether of polyethylene glycol having a molecular weight of 500–1000 diethyl ether of polypropylene qlycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate. diisodecyl azelate, dioctyl phthalate, didecyl phthalate dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl) silicate, tetra-(4-methyl-2-ethylhexyl) silicate, tetra-(p-tertbutylphenyl) silicate, hexa-(4-methyl-2-pentoxy)disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Generally the lubricants of the present invention contain a lubricating improving amount of one or more of the compositions of this invention, e.g., sufficient to provide it with improved detergent/dispersant and/or V.I. properties. Normally the amount employed will be about 0.05% to about 20%, preferably about 0.1% to about 10% of the total weight of the lubricating composition. This amount is exclusive of solvent/diluent medium. In lubricating compositions operated under extremely adverse conditions, such as lubricating compositions for marine diesel engines, the metal salts of this invention may be present in amounts of up to about 3o% by weight or more, of the total weight of the lubricating composition.

The invention also contemplates the use of other additives in combination with the compositions of this invention. Such additives include, for example detergents and dispersants of the ash-producing or ashless type, corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature about 50° C. and filtering the resulting mass. The use of a "promoter" in the neutralization step to aid the incorporation of a large excess of metal likewise is known. Examples of compound useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol sulfurized dipentene and sulfurized terpene; phosphosulfurized hydrocarbons such as the reaction product of a phosphorus sulfide with turpentine or methyl oleate,phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl napthyl phosphite, oleyl 4-pentylphenyl phosphite, polypropylene (molecular weight 500)-substituted phenyl phosphite, diisobutyl-substituted phenyl phosphite: metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents and corrosion-/oxidation inhibitors also serve as antiwear agents. Zinc dialkylphosphorodithioates are a well known example.

pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co. publishers, Cleveland, Ohio, 1967).

Examples of useful pour point depressants are polymethacrylates polyacrylates; polyacrylamides; condensation products of haloparaffin waxes and aromatic compounds: vinyl carboxylate polymers: and terpolymers of dialkylfumarates, vinylesters of fatty acids and alkylvinylethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Henry T. Kerner (Noyes Data Corporation, 1976), pages 125-162.

The compositions of this invention can be added directly to, the fuels or lubricants. Preferably, however, they are diluted with a substantially inert, normally liquid organic diluent such as mineral oil, naphtha, benzene, toluene or xylene, to form an additive concentrate. These concentrates usually contain from about 10% to 80% by weight of the composition of this invention, and 2o% to 9o% by weight of the inert diluents. The concentrates also may contain one or more other additives known in the art or described hereinabove.

The fuel compositions of the present invention contain a major proportion of a normally liquid fuel, usually a hydrocarbonaceous petroleum distillate fuel such as motor gasoline as defined by ASTM Specification D439 and diesel fuel or fuel oil as defined by ASTM Specification D396. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol and of diesel fuel and ether. Particularly preferred is gasoline, that is, a mixture of hydrocarbons having an ASTM distillation range from about 60° C. at the 10% distillation point to about 205° C. at the 90% distillation point.

Generally, these fuel compositions contain an amount of the fuel additive of this invention sufficient to improve one or more properties of the fuel such as rust-inhibition dispersancy, etc.; usually this amount is about 0.005% to about 0.5% by volume, preferably about 0.01% to about 0.2% and advantageously about o.01% to about 0.1% by volume based on the volume of such fuel compositions.

The fuel compositions can contain, in addition to the fuel additive compositions of this invention, other additives which are well known to those of skill in the art. These include antiknock agents such as tetraalkyl lead compounds, lead scavengers such as haloalkanes (e.g., ethylene dichloride and ethylene dibromide), deposit preventers or modifiers such as triaryl phosphates, dyes, cetane improvers, antioxidants such as 2,6-di-tertiary-butyl-4-methylphenol, rust inhibitors such as alkylated succinic acids and anhydrides, bacteriostatic agents, gum inhibitors, metal deactivators, demulsifiers, upper cylinder lubricants and anti-icing agents.

The fuel additive compositions of this invention can be added directly to the fuel, or they can be diluted with a substantially inert, normally liquid organic diluent such as naphtha, benzene, toluene, xylene or a normally liquid fuel as described above, to form an additive concentrate. These concentrates generally contain from about 20% to about 90% by weight of the composition of this invention and may contain, in addition one or more other conventional additives known in the art or described hereinabove.

The fuel additive compositions of this invention can be provided in concentrate form with less than the above-indicated levels of additives, and then be added directly to the fuel along with additional amounts of the compositions of this invention and other known additives, or be further diluted with additives prior to the addition to the fuel until the level of additives is at the desired level.

The following examples illustrate the concentrates and lubricating compositions of the invention. Unless otherwise indicates, all parts and percentages are by weight.

CONCENTRATE A

A concentrate is prepared by blending at room temperature, 85 parts of the product of Example A and 15 parts of motor gasoline.

CONCENTRATE B

A concentrate is prepared by blending at room temperature, 50 parts of the product of Example E and 50 parts of motor gasoline.

CONCENTRATE C

A lubricating oil concentrate prepared by blending 70 parts of the product of Example A and 30 parts of mineral lubricating oil.

CONCENTRATE D

A concentrate is prepared by blending 60 parts of the product of Example 1, and 40 parts of mineral lubricating oil.

Typical lubricating compositions according to the invention are illustrated in the following table.

TABLE

| Lubricant Example | Mineral Oil* (%) | Additive Example | Amount (%) |
|---|---|---|---|
| E | 95 | A | 5 |
| F | 98 | E | 2 |
| G | 98 | 1 | 2 |
| H | 99 | 44 | 1 |
| I | 99 | 48 | 1 |

*100 neutral base.

The lubricants identified above as Examples E through I can be modified by the inclusion of other additives normally used in lubricating oil compositions such as anti-oxidants, extreme pressure agents, anti-foam agents, etc.

We claim:
1. A method for preparing substituted carboxylic acids or derivatives thereof, which comprises:
 (i) reacting at a temperature of about 100°-200° C., a mixture of
  (A) an aliphatic polymer of a lower olefin with
  (B) an acidic reactant selected from the group consisting of fumaric acid; itaconic acid; maleic acid; and the anhydrides, lower alkyl esters, acyl chlorides and acyl bromides of any of these acids, the reacting being carried out in the presence of about 0.05 to 0.15 equivalent of chlorine per equivalent of (a) until all of the chlorine has reacted to provide a first intermediate product;

(ii) continuing the reaction in the absence of chlorine at a temperature of from about 180°–250° C. until a conversion of 0.4 to 1.1 equivalents of (B) per equivalent of (A) is attained to provide a second intermediate product; and (iii) reacting said second intermediate with about 0.2 to 1.5 equivalents of chlorine per equivalent of (A) used in step (i) at a temperature of about 180°–225° C.

2. The method according to claim 1 comprising introducing the chlorine in step (i) over a period of time while increasing the temperature of the mixture to a temperature of up to 200° C.

3. The method according to claim 1 further comprising heating the mixture of (A) and (B) to a temperature of from about 80°–120° C., and thereafter in step (i) introducing the chlorine continuously while increasing the temperature of the reaction mixture to about 200° C., and maintaining this temperature until all of the chlorine has reacted.

4. The method according to claim 1 wherein the reaction in step (ii) is continued until a conversion of 0.5 to 0.9 equivalents of (B) per equivalent of (A) is attained.

5. The method according to claim 1 wherein about 0.3 to about 1.0 equivalent of chlorine is used in step (iii) per equivalent of (A) used in step (i).

6. The method according to claim 1 wherein the first intermediate product is characterized by a conversion of up to 0.2 equivalent of (B) per equivalent of (A).

7. The method according to claim 1 wherein the aliphatic polymer (A) has a number average molecular weight in the range of about 500 to 3000.

8. The method according to claim 7 wherein the polymer is polyisobutene.

9. The method according to claim 1 wherein the acidic reactant (B) is maleic anhydride.

10. The method according to claim 1 wherein the ratio of equivalents of (A) to (B) is from about 1:0.8 to about 1:2.

11. A method for preparing hydrocarbon substituted succinic anhydrides, which comprises:

(i) reacting at a temperature of about 100°–200° C., a mixture of
(A) at least one aliphatic polymer of a lower olefin with
(B) maleic anhydride, the reacting being carried out in the presence of about 0.05 to 0.15 equivalent of chlorine per equivalent of maleic anhydride until no additional hydrogen chloride is evolved to provide a first intermediate product;

(ii) continuing the reaction in the absence of chlorine at a temperature of from about 180°–250° C. until a conversion of about 0.5 to 0.85 equivalent of maleic anhydride per equivalent of (A) is attained to provide a second intermediate product; and (iii) reacting said second intermediate product with from about 0.2 to 1.0 equivalent of chlorine per equivalent of (A) used in step (i) at a temperature of about 180°–225° C.

12. The method according to claim 11 wherein the aliphatic polymer is polyisobutene.

13. The method according to claim 12 wherein the polyisobutene has a number average molecular weight of from about 500 to 3000.

14. The method according to claim 11 wherein the first intermediate product is characterized by a conversion of up to 0.2 equivalent of maleic anhydride per equivalent of (A).

15. The method according to claim 11 comprising introducing the chlorine continuously in step (i) while increasing the temperature of the reaction mixture from about 100° C. to about 190° C. and thereafter maintaining the mixture at this temperature until there is no additional hydrogen chloride evolved.

16. The method according to claim 11 wherein the reaction in step (ii) is conducted in an inert atmosphere.

* * * * *